(12) United States Patent
Boyer, II et al.

(10) Patent No.: US 8,388,657 B2
(45) Date of Patent: *Mar. 5, 2013

(54) SPINOUS PROCESS SPACER

(75) Inventors: Michael Lee Boyer, II, Phoenixville, PA (US); Paul W. Millhouse, Wayne, PA (US); David C. Paul, Phoenixville, PA (US)

(73) Assignee: Globus Medical, Inc, Audubon, PA (US)

( * ) Notice: Subject to any disclaimer, the term of this patent is extended or adjusted under 35 U.S.C. 154(b) by 322 days.

This patent is subject to a terminal disclaimer.

(21) Appl. No.: 12/904,515

(22) Filed: Oct. 14, 2010
(Under 37 CFR 1.47)

(65) Prior Publication Data
US 2011/0125191 A1    May 26, 2011

Related U.S. Application Data

(63) Continuation of application No. 11/366,388, filed on Mar. 3, 2006, now Pat. No. 7,837,688.

(60) Provisional application No. 60/689,532, filed on Jun. 13, 2005.

(51) Int. Cl.
*A61B 17/70* (2006.01)
(52) U.S. Cl. .................................................. 606/249
(58) Field of Classification Search .......... 606/246–249, 606/279, 86 A, 914; 623/17.16
See application file for complete search history.

(56) References Cited

U.S. PATENT DOCUMENTS

2006/0184248 A1 * 8/2006 Edidin et al. ............... 623/17.11

* cited by examiner

*Primary Examiner* — Sameh Boles

(57) ABSTRACT

Interspinous process implants are disclosed. An Implant is adapted and configured to be placed between adjacent spinous processes. Implant is generally H-shaped or anvil shaped with a saddle portion or central support portion extending laterally along axis between lateral end portions. End portions partially protrude beyond the front and back surfaces of support portion thereby creating a slight indentation along the front and back or anterior and posterior of central portion.

19 Claims, 25 Drawing Sheets

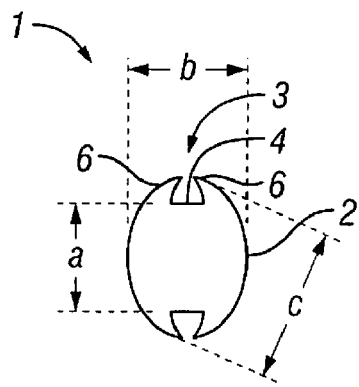
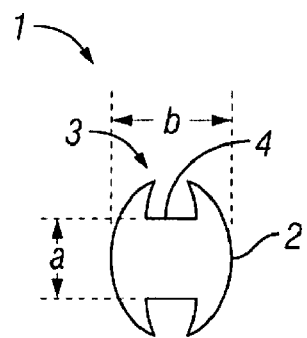
FIG. 1A
FIG. 1B
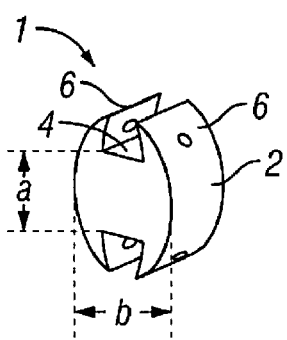
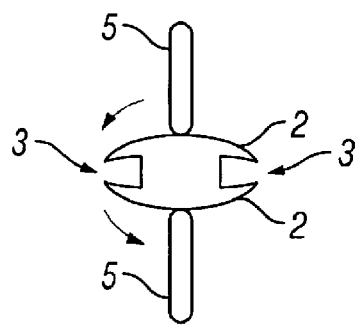
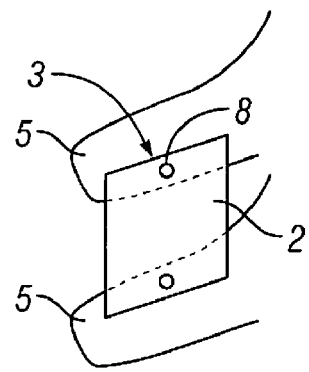
FIG. 1C
FIG. 1D
FIG. 1E
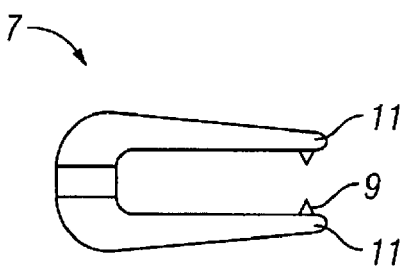
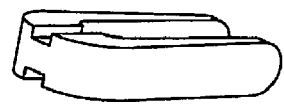
FIG. 1F
FIG. 1G

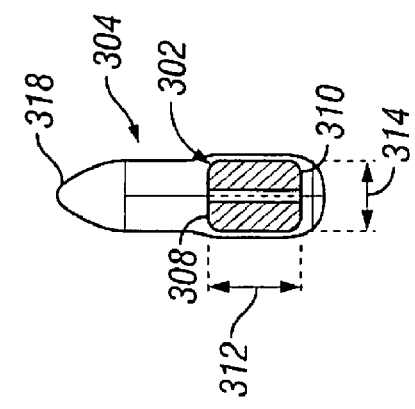
FIG. 30
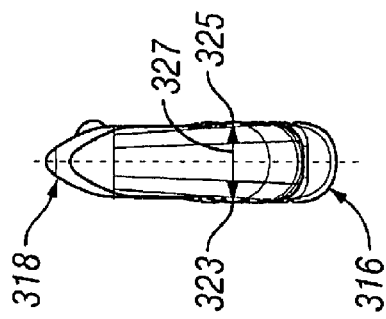
FIG. 33
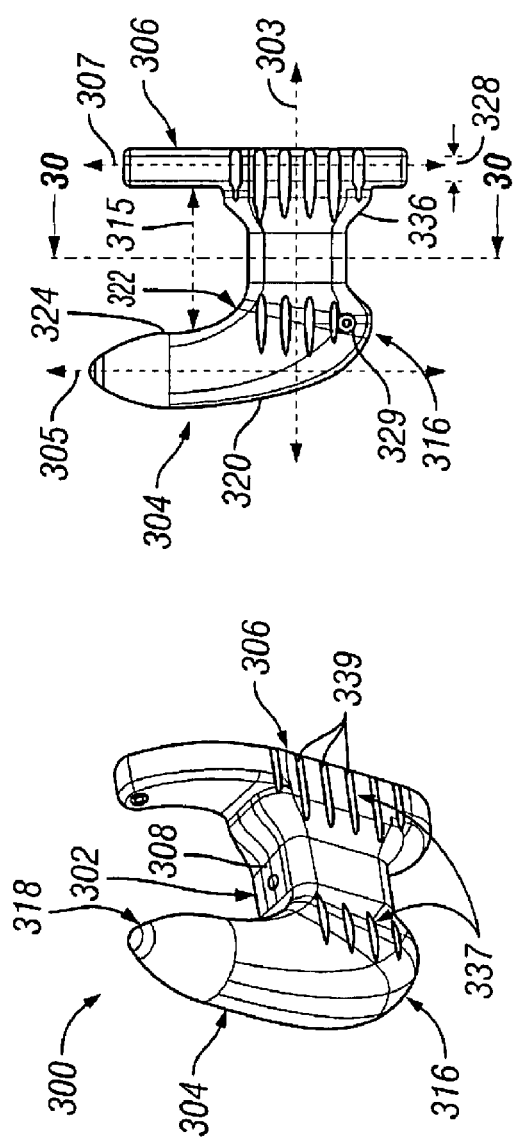
FIG. 29
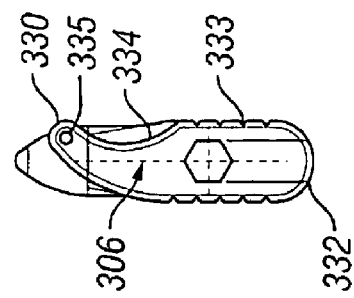
FIG. 32
FIG. 28
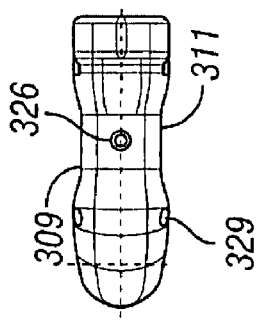
FIG. 31

SPINOUS PROCESS SPACER

CROSS REFERENCE TO RELATED APPLICATIONS

The present application is a continuation application claiming priority to U.S. patent application Ser. No. 11/366,388 filed on Mar. 3, 2006, now U.S. Pat. No. 7,837,688, which claims priority to U.S. Provisional Patent Application Ser. No. 60/689,532 filed on Jun. 13, 2005, the entire contents of which are incorporated herein by reference.

FIELD OF THE INVENTION

The present invention is generally directed to interspinous process implants, systems and kits including such implants, methods of inserting such implants, and methods of treating spinal stenosis or for alleviating pain or discomfort associated with the spinal column.

BACKGROUND OF THE INVENTION

Occurrences of spinal stenosis are increasing as society ages. Spinal stenosis is the narrowing of the spinal canal, lateral recess or neural foramen, characterized by a reduction in the available space for the passage of blood vessels and nerves. Clinical symptoms of spinal stenosis include extremity pain, radiculopathy, sensory or motor deficit, bladder or bowel dysfunction, and neurogenic claudication. Pain associated with such stenosis can be relieved by surgical or non-surgical treatments, such as medication, physical therapy, back braces and the like.

There is a need for implants that may be placed between spinal processes for minimally invasive surgical treatment of spinal stenosis.

SUMMARY OF THE INVENTION

The present invention is directed to minimally invasive implants, in particular, interspinous process implants or spacers. The invention is further directed to systems and kits including such implants, methods of inserting such implants, and methods of alleviating pain or discomfort associated with the spinal column.

The present invention provides spacers or implants and methods for relieving pain and other symptoms associated with spinal stenosis, by relieving pressure and restrictions on the blood vessels and nerves. Such alleviation of pressure may be accomplished in the present invention through the use of an implant placed between the spinous process of adjacent vertebra. While the implants and methods of the invention particularly address the needs of the elderly, the invention can be used with individuals of all ages and sizes where a spacer between spinous processes would be beneficial.

In certain aspects of the invention, various implants are provided for creating, increasing, or substantially maintaining a desired distraction or spacing between a first spinous process and a second spinous process (adjacent spinous processes). In another aspect of the invention, implants may be extended to create, increase or substantially maintain a desired distraction or spacing of more than two adjacent spinous processes.

In another aspect of the invention, implants in accordance with the present invention may be attached to one or more spinous processes or other portion of the spine, or may attach to itself in such a manner as to secure the implant between two adjacent spinous processes. In yet other aspects of the invention, implants in accordance with the present invention may be secured in place with respect to spinous processes by mechanical forces resulting from the design of the implant or attachments to the implant, and/or surface modifications thereto.

In another aspect of the present invention, methods are provided for treating spinal stenosis. In yet further aspects of the invention, methods are provided for inserting implants. These methods may include implanting a device to create, increase, or maintain a desired amount of distraction between adjacent first and second spinous processes. Methods may include creating an incision in a patient, removing any interspinous ligaments in a position in which the implant is to be placed in the patient, sizing the space between adjacent spinous processes, and inserting an implant of the appropriate size between the spinous processes. In another aspect of the invention, methods may further include securing the implant. In another aspect of the invention, methods of the present invention may include distracting the spinous processes apart from one another before sizing and/or before inserting the implant.

In a further aspect of the invention kits are provided that include one or more implants, and optionally any tools or devices that may be required or useful in inserting the implant into a patient, such as tools or devices that may be useful in distracting spinous processes, and/or selecting, inserting, positioning, and/or securing one or more implants.

In a further aspect of the invention systems are provided that include at least one implant and at least one fastening device. Systems in accordance with the present invention may further include one or more of the following: a tool or device for removing any interspinous ligaments in the way of inserting the implant; a tool or device for sizing the space between adjacent spinous processes; and a tool or device for distracting spinous processes, and/or selecting, inserting, positioning, and/or securing one or more implants.

BRIEF DESCRIPTION OF THE DRAWINGS

The invention will be more readily understood with reference to the embodiments thereof illustrated in the attached figures, in which:

FIGS. 1a-1b depict one embodiment of an implant according to the present invention for creating, increasing, or maintaining distraction between adjacent spinous processes;

FIG. 1c is a perspective view of the implant of FIGS. 1a and 1b;

FIG. 1d is a side view of the implant of FIGS. 1a-1c shown in a first implantation position in relation to the spinous processes between which the implant is implanted;

FIG. 1e is a side view of the implant of FIGS. 1a-1c shown in a second implantation position in relation to the spinous processes between which the implant is implanted;

FIG. 1f depicts a stapler that may be used to secure an implant to one or more spinous processes;

FIG. 1g depicts a device that may be used to determine a space between spinous processes and/or a desired size or shape of implant to be used;

FIG. 6b depicts a front view of the implant according to FIG. 6a;

FIG. 27b depicts a side view of the center portion of FIG. 27a;

FIG. 28 is a perspective view of another embodiment of an implant according to the present invention for creating, increasing, or maintaining distraction between adjacent spinous processes;

FIG. 29 is a front view of the implant of FIG. 28;

FIG. 30 is a cross-sectional view of the implant of FIG. 29 taken along line 30-30;

FIG. 31 is a bottom view of the implant of FIGS. 28-30;

FIG. 32 is an end view of the implant of FIGS. 28-31;

FIG. 33 is another end view of the implant of FIGS. 28-32;

DETAILED DESCRIPTION OF THE INVENTION

Figure 2:
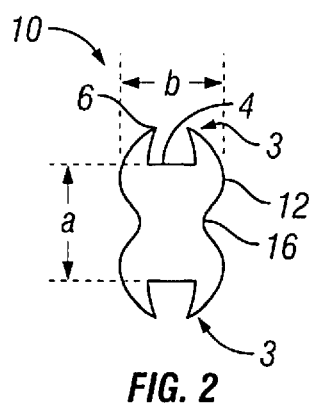
FIGS. 2 and 3a-3c depict implants according to other embodiments of the present invention.

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Implants

The present invention is directed to minimally invasive implants, in particular, interspinous process spacers. Implants in accordance with the present invention may come in many shapes and sizes. The illustrative embodiments provided herein-below provide guidance as to the many types of implants that may be advantageously used in accordance with the present invention. In particular, the implants of the present invention are adapted such that their insertion technique (including methods of the present invention) is minimally invasive, simpler, and/or safer than previously discussed techniques. Implants according to the present invention may be advantageously inserted into a patient as an out-patient procedure.

Embodiments of the present invention include implants adapted to be placed between first and second adjacent spinous processes. The implants may be adapted such that after insertion of an implant into a patient, a portion of the implant maintains a desired amount of distraction or spacing between two adjacent spinous processes. The implants or portions thereof that substantially maintain a desired spacing between spinous processes are also referred to herein as "spacers." In various embodiments described herein, the implants may include spinous process support surfaces, indented portions or saddle portions spaced apart by a distance (a), which corresponds to a desired distance for distraction or spacing of two adjacent spinous processes. Other embodiments similarly provide a desired distance for distraction or spacing of two adjacent spinous processes. Depending on the material and/or design of the implant, the desired distraction or spacing distance may vary somewhat after insertion, for example if a patient moves its spine into a position that causes further distraction. For example, in certain embodiments the implant may be resiliently compressible or expandable in the cranial-caudal direction such that the implant may support and or adjust to dynamic movement of the spine. Although not depicted in the figures discussed below, it is contemplated that embodiments of the present invention may be extended to provide distraction or spacing of more than two adjacent spinous processes.

Implants in accordance with the present invention may be attached to one or more spinous processes or other portion of the spine, or may attach to itself in such a manner as to secure the implant between two adjacent spinal processes. By way of example, implants in accordance with the present invention may be attached to one or both spinous processes or other portion of the spine (see e.g., FIGS. 22-24) by one or more pins, screws, wires, cables, straps, surgical rope, sutures, elastic bands, or other fastening devices. Alternatively implants of the present invention may secure themselves in place without a fastening device attached directly to a spinous process or other portion of the spine (see e.g., FIGS. 19-21). "Securing" implants between spinous processes, does not require that the implant not move at all, but rather means that the implant does not move so far away from between the spinous processes that it does not perform the function of maintaining a desired distraction distance or space between the adjacent spinous processes.

Implants in accordance with the present invention may be secured between spinous processes by methods other than using a fastening device. For example, according to certain embodiments, implants in accordance with the present invention may be secured in place with respect to spinous processes by mechanical forces resulting from the design of the implant, including the shape itself. Exemplary implants may also be secured to spinous processes, by surface modifications to portions of the implant, such as to create frictional forces or other bonds between the implant and spinous processes. Such surface modifications may include mechanical modifications to the surface (see e.g., spikes in FIG. 16) and/or one or more coatings. Such mechanical forces and/or surface modifications may be utilized in addition to, or in place of various other attachment methods described herein.

Implants in accordance with the present invention may be made of one or more materials suitable for implantation into the spine of a mammalian patient. Materials in accordance with the present invention may be biocompatible with a mammalian patient and/or may have one or more surface coatings or treatments that allow the spacers to be biocompatible. Materials in accordance with the present invention may include one or more materials having sufficient load capability and/or strength to maintain the desired spacing or distraction between spinous processes. Depending on the design employed, certain embodiments may have components or portions made of a material having certain flexibility, as desired for the particular application. Additionally, the materials of the present invention may be made of one or more materials that maintain their composition and shape for as long a time as possible without degrading or decomposing or changing shape, such that replacement of the implant is avoided.

Suitable materials for use in accordance with the present invention would be known to those skilled in the art. Non-limiting examples include one or more materials selected from titanium, polyetheretherketone (PEEK), ceramics, deformable materials, bone, allograft, demineralized or partially demineralized bone, allograft ligament, and polyurethane (for example, for portions of the insert where cushioning is desired). Similarly, any fastening devices may be made of materials having one or more of the properties set forth with respect to the implant itself. For example, screws or pins may include titanium and straps may include polyethylene. In some embodiments, primarily radiolucent material may be used. In this regard, radio-opaque material or markers may be used in combination with the radiolucent material to facilitate implantation. Exemplary radio-opaque material includes but is not limited to titanium alloys, tantalum or other known radio-opaque marker material. As indicated above, implants in accordance with the present invention may have one or more portions that may have modified surfaces, surface coatings, and/or attachments to the surface, which may assist in maintaining the spacer in a desired position, for example by friction. Suitable surface modifications, coatings, and attachment materials would be known to those skilled in the art, taking into consideration the purpose for such modification, coating, and/or attachment.

Implants according to the present invention may be adapted to be inserted between a first and second spinous process at any region in the spine. Although typically implants according to the present invention may be inserted in the lumbar region, it is contemplated that it is possible to configure inserts according to the present invention for insertion into other regions such as for example, the thoracic or cervical region. In general, implants according to the invention may have varying profiles when viewed in a saggital plane. In this regard, the implants can have varied cross-sectional shapes to conform to the varied anatomical shapes of the interspinous spaces of the spine.

Methods for Treating Stenosis and Methods of Inserting an Implant

Methods are provided for treating spinal stenosis. Methods are also provided for inserting an implant. These methods may include implanting a device to create, increase, or maintain a desired amount of distraction, space, or distance between adjacent first and second spinous processes. The adjacent first and second spinal processes may be accessed by various methods known by practitioners skilled in the art, for example, by accessing the spinous processes from at least one lateral side/unilateral, bilateral, or midline posterior approach.

Certain methods of the present invention include creating an incision in a patient to be treated, removing/dilating any interspinous ligaments in a position in which the implant is to be placed in the patient, sizing the space between adjacent spinous processes (for example using trials), and inserting an implant of the appropriate size between the adjacent spinous processes. Methods of the present invention may include securing the implant to one or more of the spinous processes, to one or more other portions of the patient's spine, and/or to itself such that the implant maintains its position between the spinous processes.

Methods of the present invention may include dilating or distracting the spinous processes apart from one another before sizing and/or before inserting the implant. Methods may vary depending on which implant is being inserted into a patient. For example, certain implants may require distracting the spinous processes apart before inserting the implant, while other implants may themselves dilate or distract the spinous processes while inserting the implant. In embodiments where the implants themselves dilate or distract the spinous process, the implant may have, for example, a predetermined shape to dilate, distract, or otherwise move or separate apart adjacent spinous processes such as a cam or cam-like profile, it may have a distraction device that is deployed, and/or it may have a tapered expander to distract an opening between the adjacent spinous processes or other features to facilitate distraction of the adjacent spinous processes.

According to certain embodiments, spacers may be placed between the spinous processes anterior to the supraspinous ligament, avoiding the nerves in the spinal canal. The procedure may be performed under local anesthesia. For surgical procedures, in which an implant is being inserted into the lumbar region, the patient may be placed in the right lateral decubitus position with the lumbar spine flexed.

According to certain embodiments, one or more probes may be used to locate the space between the spinous processes. Depending on the design of the spacer to be inserted, the space may be widened, for example with a dilator before inserting the implant.

While the present invention is satisfied by embodiments in many different forms, there will herein be described in detail embodiments of the invention, with the understanding that the present disclosure and examples are to be considered as exemplary and/or illustrative of the principles of the invention and are not intended to limit the scope of the invention to the embodiments illustrated and described. As would be apparent to skilled artisans, various changes and modifications are possible and are contemplated within the scope of the invention described, and may be made by persons skilled in the art without departure from the spirit of the invention.

Systems and Kits

Kits in accordance with the present invention may include one or more implants. For example, kits having at least one implant such as those depicted in FIG. 1a-1d or 2, may include various sizes of implants having varying distances (a), for example incremental distances, such as 2 mm increments.

Kits in accordance with the present invention may further include one or more tools or other devices that may be useful in distracting spinous processes, and/or selecting, inserting, positioning, and/or securing one or more implants. By way of non-limiting example, such tools and/or devices may include one or more of the following: those adapted to remove/dilate interspinous ligaments in the way of inserting the implant into the patient; those for sizing the space between adjacent spinous processes such as one or more trials of varying or various sizes (see e.g., the device depicted in FIG. 1g); those for inserting an implant between adjacent spinous processes; those for distracting the spinous processes apart from one another; and those for securing one or more implants between adjacent spinous processes.

Tools or devices for distracting the spinous processes may be adapted for example, to provide for distraction in the range of about 5 mm to about 15 mm. However, devices that can distract up to and above 22 mm may be used depending on the characteristics of the patient.

Tools and devices that may be used to secure one or more implants between spinous processes may include for example, one or more pins, screws, wires, cables, straps, surgical rope, sutures, or other fastening devices, and/or tools for inserting, securing or tightening such fastening devices. For example, a stapler such as that depicted in FIG. 1f may be used in some embodiments to secure an implant such as that depicted in FIGS. 1a-1e.

In a further aspect of the invention, systems may be provided that include at least one implant and at least one fastening device. Systems in accordance with the present invention may further include one or more of the following: one or more tools or devices for removing any interspinous ligaments in the way of inserting the implant; one or more tools or devices for sizing the space between adjacent spinous processes; and one or more tools or devices for distracting spinous processes, and/or selecting, inserting, positioning, and/or securing one or more implants.

Further non-limiting examples of implants, methods, kits and systems in accordance with the present invention are set forth below with respect to the described implant embodiments.

Referring now to FIGS. 1a-1e, one exemplary embodiment of an implant 1 according to the invention is shown for creating, increasing, or maintaining distraction between adjacent spinous processes. In general, implant 1 is adapted and configured to be placed between adjacent spinous processes. For example, referring to FIGS. 1d and 1e, a side view of implant 1 is shown in implanted positions in relation to two adjacent spinous processes 5 between which the implant is implanted. As best seen in FIGS. 1a-1c, implant 1 is a unitary body with a general oval, ovoid, oblong, football-like shape and generally includes at least one rounded lateral side surface or portion 2, and two or more indented portions, troughs, or saddle portions 3 adjacent the longitudinal ends. In one embodiment, implant 1 comprises two rounded lateral side surfaces or portions 2. Saddle portions 3 are generally configured and dimensioned to engage the spinous processes 5 and each generally includes a saddle surface 4 with tines or walls 6 extending longitudinally beyond the lateral sides thereof. Saddle surfaces 4 are spaced longitudinally apart by a distance (a), which generally corresponds to the desired distance for distraction or spacing of two adjacent spinous processes 5. Implant 1 has a maximum lateral width (b) measured between the outermost point or section of the lateral side surfaces or portions 2. The distance (a) may vary with respect to distance (b) and in a preferred embodiment distance (a) is greater than distance (b). According to certain embodiments distance (a) may be proportional to distance (b). Non-limiting examples of distance (a) may include any distance from about 3 mm to about 25 mm or from about 7 mm to about 21 mm.

Walls 6 are generally spaced in the lateral direction a sufficient distance to accommodate the width of a spinous process therebetween and walls 6 may contact or engage the lateral sides of the spinous process when the implant is implanted. In this regard, walls 6 generally prevent or limit lateral movement of the implant when the implant is implanted, such as for example when in the position shown in FIG. 1e.

In certain variations of the present embodiment, implant 1 may be attached to one or both of the adjacent spinous processes to secure the implant. By way of non-limiting example, the implant may have openings 8, which permit the attachment of the implant to one or both spinous processes by one or more fastening devices. As discussed above, according to certain embodiments, implants in accordance with the present invention may be secured in place with respect to spinous processes by mechanical forces resulting from the design of the implant, including the shape itself. In other embodiments, implant 1 may also be secured to spinous processes, by surface modifications to portions of the implant, such as modifications to the inner surfaces of walls 6 to create frictional forces or other bonds between the implant and spinous processes. Such surface modifications may include mechanical modifications to the surface and/or one or more coatings. Such mechanical forces and/or surface modifications may be utilized in addition to, or in place of (in which case, the implant may have no openings 8) various other attachment methods described herein.

FIG. 2 exemplifies another implant 10 according to the present invention adapted to be placed between adjacent spinous processes. Implant 10 comprises at least one rounded lateral side surface or portion 12, and two or more indented portions, troughs, or saddle portions 3. Implant 10 of FIG. 2 is similar to implant 1 of FIG. 1, except that the lateral side surface(s) or rounded portion(s) 12 may include one or more portions 16 that modify the curve of the rounded portion(s) 12. In this embodiment, portion 16 reflects a concave section positioned between convex sections of rounded portion(s) 12. In alternate embodiments, lateral side surfaces or portions 12 may have differing shapes other than simple curves that may facilitate rotation in situ and/or provide additional mechanical advantage to distract the spinous processes in operation. Similar to implant 1, the saddle portions 3 are spaced apart by a distance (a), which generally corresponds to the desired distance for distraction or spacing of two adjacent spinous processes.

According to methods of the present invention, implants 1, 10 may be inserted between two adjacent spinous processes 5 wherein a portion of at least one rounded portion 2, 12 may contact at least one of the adjacent spinous processes as shown, for example in FIG. 1*d* for implant 1, and the implant may be rotated until the two adjacent spinous processes are positioned into the saddle portions 3 of the implant, as shown in FIG. 1*e*.

The implant itself may serve to dilate or distract the spinous processes as it is being inserted and/or after insertion. For example, in embodiments in which the implant is similar to that depicted in FIGS. 1 and 2, the implant may be initially inserted laterally between the compressed adjacent spinous processes as shown in FIG. 1*d*. The supraspinous ligament may or may not be removed. In an initial pre-implantation condition, the adjacent spinous process may be compressed such that the initial space or longitudinal distance between the processes may be equal to or smaller than distance (b) of implant 1. During lateral insertion of the implant, one or more lateral side surfaces or portions 2, 12 of the implant may contact one or both of the spinous processes 5 and may initially distract the processes a distance (b). As the implant is inserted further between the spinous processes and rotated, the rounded portion(s) may distract the spinous processes further apart from one another, until the implant is rotated into a longitudinal or implanted position and the spinous processes are fitted into the saddle portions 3 of the implant. In operation, lateral side surfaces or portions 2, 12 of implants 1, 10 engage the adjacent spinous processes as the implant is rotated to act or perform in a cam-like manner to translate the rotational force to separate the spinous processes in the longitudinal or cranial-caudal direction as the implant is rotated. In one embodiment, implants 1, 10 may be rotated about 90 degrees or from the horizontal or lateral position to the vertical or longitudinal position. The maximum distraction of spinous processes by the implant is distance (c) depicted in FIG. 1*a*. Once the implant is implanted and after the spinous processes are fitted into the saddle portions 3 of the implant, the implant may maintain the spinous processes in a distracted or spaced condition, for example where the distance (a) of the implant is greater than a pre-implantation distance between the spinous processes.

Kits having at least one implant such as those depicted in FIGS. 1 and 2, may include various sizes of implants having varying distances (a), for example incremental distances, such as 2 mm increments.

Tools and devices that may be used to secure one or more implants between spinous processes may include for example, one or more pins, screws, wires, cables, straps, surgical rope, sutures, or other fastening devices, and/or tools for inserting, securing or tightening such fastening devices. For example, a staple device 7 such as that depicted in FIG. 1*f* may be used to secure an implant such as those depicted in FIGS. 1*a*-1*e*. Staple device 7 may be used to crimp the implant in place, create holes in the spinous process in alignment with openings 8 to facilitate insertion of alternate fastening devices, and/or clasp the implant to the spinous process and remain in-situ. The following is a non-limiting example of how such a staple device may be used. Pins, screws or other fastening devices 9 at the open ends 11 of the staple device may be aligned adjacent to the openings 8 of the implant on either side of a spinous process after the implant is positioned with respect to the spinous processes. The open ends 11 of the staple device are then compressed together such that the fastening devices 9 secure the implant to the spinous process through openings 8 of the implant.

Figure 3A:
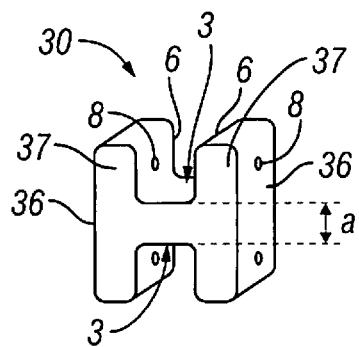
Figure 3B:
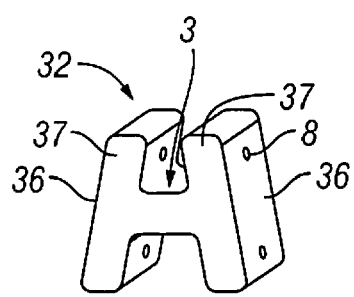
Figure 3C:
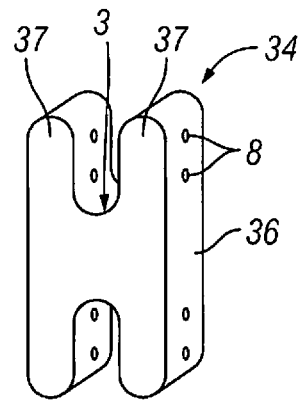

Referring to FIGS. 3*a*-3*c*, additional embodiments of implants according to the present invention adapted to be placed between adjacent spinous processes are shown. Implants 30, 32, and 34 generally comprise at least one substantially straight lateral side surface or portion 36, and two or more indented portions, troughs, or saddle portions 3 adjacent the longitudinal ends. Each of the straight side portions 36 may include proximal ends 37 and distal ends 38 that are rounded such as shown in FIG. 3*c* with respect to implant 32, or squared such as shown in FIG. 3*a* with respect to implant 30. In embodiments having more than one straight portion 36, in one variation at least two of the straight portions may be substantially parallel to one another, such as shown in FIG. 3*a* with respect to implant 30. In alternative embodiments, the at least two straight portions 36 may not be substantially parallel, such as shown in FIG. 3*b* with respect to implant 32 where proximal ends 37 of straight portions 36 are spaced laterally closer together than the corresponding distal ends 38 of the straight portions 36, creating a tapered configuration.

As with previous embodiments, the saddle portions 3 are spaced longitudinally apart by a distance (a), which may vary as described herein with respect to other embodiments of the invention. As with previous embodiments, walls 6 of saddle portions 3 may be spaced laterally apart a sufficient distance to allow the spinous processes to fit within the saddle portions 3. Walls 6 may also be close enough together such that when the implants are positioned such that the spinous processes are within saddle portions 3, the implant may be attached to one or both of the adjacent spinous processes. By way of example, the implant may have openings 8, which allow one to attach the implant to one or both spinous processes by one or more fastening devices or methods as described herein.

According to methods of the present invention, the implant may be inserted between two adjacent spinous processes and the implant may be rotated until the two adjacent spinous processes are positioned into the saddle portions 3 of the implant. Certain methods of the present invention include creating an incision in a patient to be treated, removing any spinous ligaments in a position in which the implant is to be placed in the patient, sizing the space between adjacent spinous processes (for example using trial blocks or spacers), and inserting an implant of the appropriate size between the adjacent spinous processes. Methods of the present invention may include distracting the spinous processes apart from one another before sizing and/or before inserting the implant. Methods of the present invention may include securing the implant to one or more of the spinous processes and/or to one or more other portions of the patient's spine, such that the implant maintains its position between the spinous processes.

The implant itself may serve to distract the spinous processes as it is being inserted and/or after insertion. For example, implant 32 of FIG. 3*b* may be inserted with the narrow or tapered end (where the ends 37 of sides 36 are laterally closer together) first. In operation, as the implant is further inserted between the spinous processes, the increasing distance between sides 36 may serve to distract the spinous processes from one another.

Figure 4A:
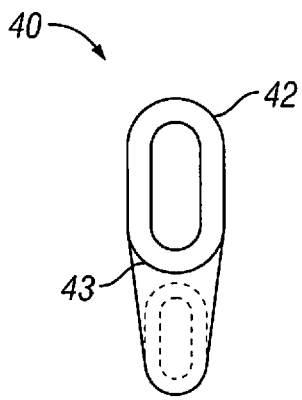
FIGS. 4a-4b depict a perspective and side view of implants according other embodiments of the present invention.
Figure 4B:
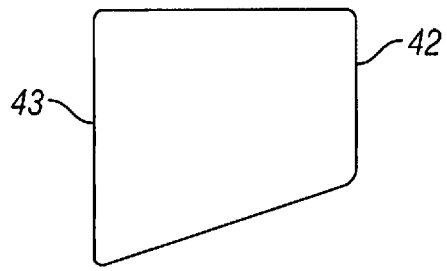

Referring to FIGS. 4*a*-4*b*, another embodiment of an implant 40 adapted to be placed between adjacent spinous processes is shown. Implant 40 generally comprises an oblong body and includes a narrow end 42 and a wide end 43 to form a wedge-like shape.

According to methods of the present invention, the implant may be inserted between two adjacent spinous processes such that the narrow end 42 is inserted first and the wedge-like shape serves to distract the spinous processes as the implant is further inserted between the spinous processes.

Referring to FIGS. 5-8, additional embodiments of implants according to the invention for creating, increasing, or maintaining distraction between adjacent spinous processes are shown. In particular, FIGS. 5-8 exemplify implants adapted to be placed between adjacent spinous processes, which generally include a main body 54 and at least two arms 56. In general, the implants may be resiliently compressible or expandable such that the implants may support and or adjust to dynamic movement of the spine. In this regard, the implants may include one or more biasing members or springs 58 or other configurations or materials that allow the body to dynamically distract less or more distance.

Figure 5:
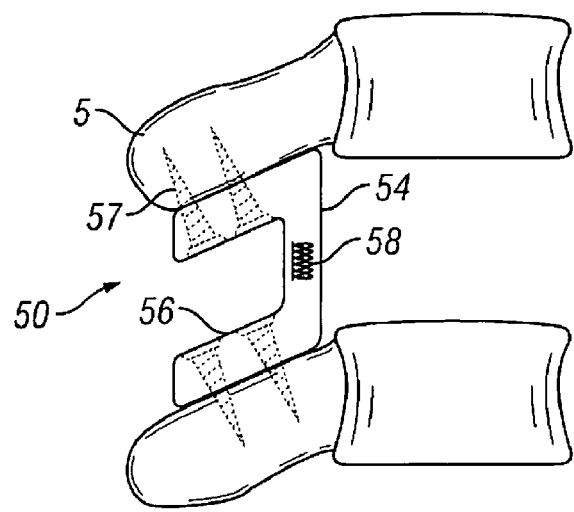
FIGS. 5, 6a, and 7 depict a side view of implants according to other embodiments of the present invention in relation to the spinal processes between which the implants are implanted, where the implants are secured to the spinous processes by a fastening device.

Referring to FIG. 5 one exemplary embodiment of an implant 50 is shown wherein the entire device is positioned between the spinous processes. In this regard, arms 56 of implant 50 are configured to contact, support, or otherwise engage the respective superior and inferior surfaces of the adjacent spinous process without contact with the lateral or side surfaces of the spinous processes: In this embodiment, implant 50 may be attached directly or secured to the superior and inferior surfaces or the spinous processes for example by one or more fastening devices 57, such as screws, as shown in FIG. 5. Biasing member or spring 58 permits arms 56 of implant 50 to resiliently compress together or expand apart in the cranial-caudal direction. In this regard, spring 58 provides dynamic support between the adjacent spinous processes and accommodates extension and flexion of the spine.

Figure 6A:
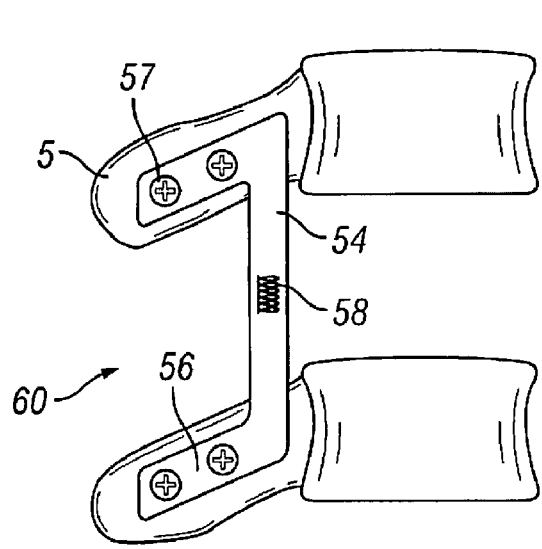
Figure 6B:
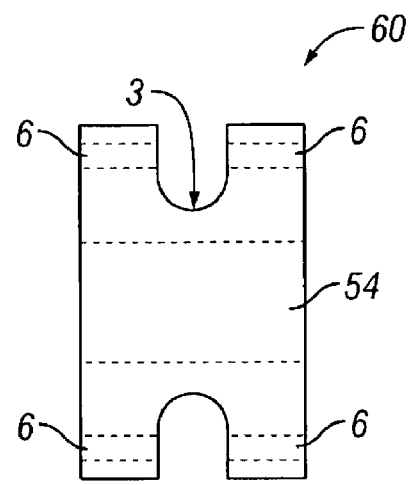

Referring to FIGS. 6*a* and 6*b*, another embodiment of an implant 60 of the present invention is shown. Implant 60 is similar to implant 50 described above, except the arms 56 or portions thereof are not entirely positioned between the spinous processes. In this embodiment, the arms 56 of implant 60 may be attached for example, to the sides of the spinous processes 5 by one or more fastening devices 57, such as screws, as depicted in FIG. 6*a*.

As best seen in FIG. 6*b*, implant 60 may include saddle portions 3 which include arms or walls 6. As depicted in FIG. 6*b*, in one embodiment implant 60 may have at least one saddle portion 3. Arms or walls 6 may be spaced laterally apart a sufficient distance to allow the spinous processes 5 to fit within the saddle portions 3. Arms or walls 6 may also be close enough together such that when the implants are positioned such that the spinous processes are within saddle portions 3, the implant may be attached to one or both of the adjacent spinous processes as discussed above and/or secured in place by virtue of its design.

Figure 7:
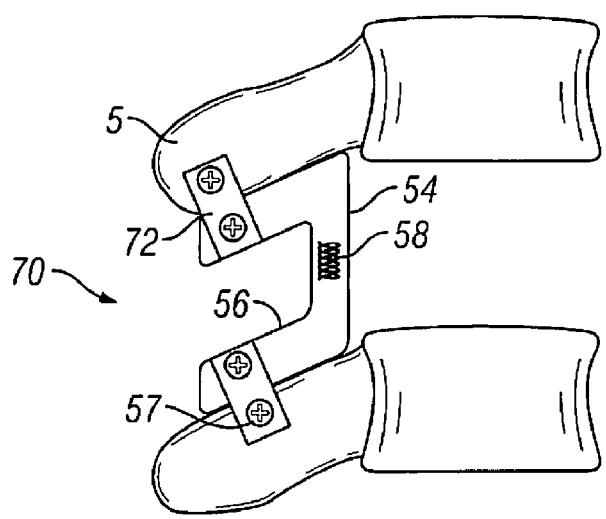
Figure 8:
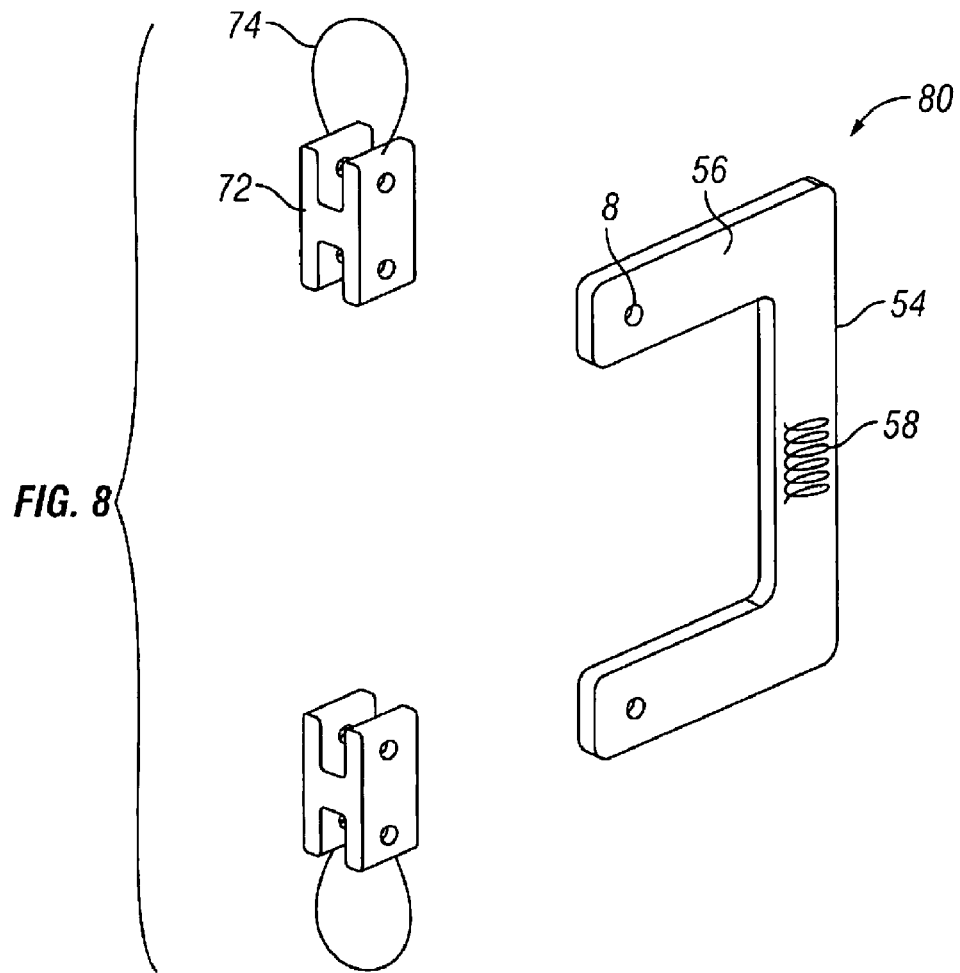
FIG. 8 depicts a side view of the implant of FIG. 7, before being implanted between spinous processes.

FIGS. 7 and 8 depict embodiments similar to those shown in FIG. 5 where the entire device is positioned between the spinous processes. The embodiments of FIGS. 7 and 8 may be attached to the spinous processes for example by one or more fastening devices 72, as shown in FIGS. 7 and 8. Fastening device 72 may be attached to an arm 56 of the implant and a spinous process 5. Optionally, a strap 74 or other fastening device may be used to further secure the implant to one or both spinous processes.

Figure 9:
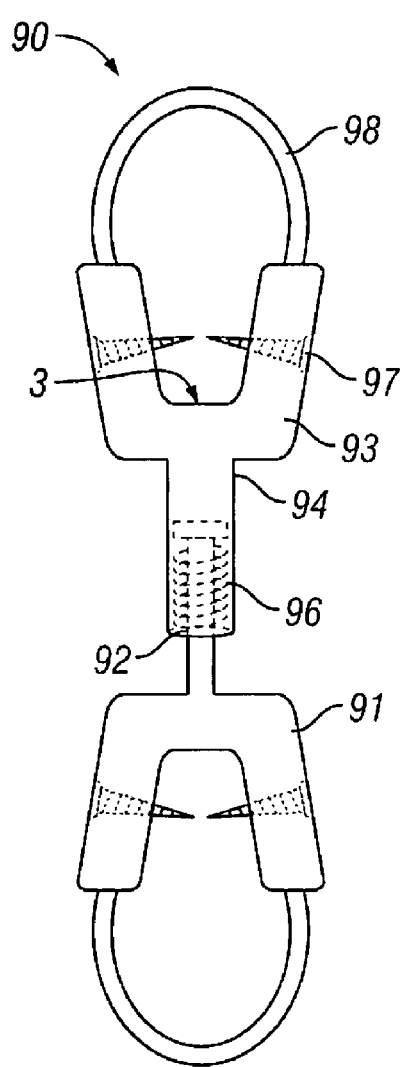
FIG. 9 depicts other embodiments of implants of the invention.

Referring to FIG. 9, another exemplary embodiment of an implant 90 according to the present invention is shown. Implant 90 generally comprises a distal or first end 91 having a first shaft 92 extending proximally therefrom and a proximal or second end 93 with a second shaft 94 extending distally therefrom. A spring 96 is positioned concentric to shaft 92 and configured and dimensioned to fit coaxially inside a substantially cylindrical opening of the second shaft 94 of second end 93. The configuration may allow implant 90 to be somewhat flexible after implantation between spinal processes, by virtue of the spring 96, which allows first end 91 and second end 93 to move further apart and closer together with respect to each other after implantation into the patient. Similar to previously described embodiments, spring 96 provides dynamic support between the adjacent spinous processes and accommodates extension and flexion of the spine.

According to other embodiments, the spring configuration facilitates implantation into the patient as it allows the first end 91 and second end 93 to be compressed together during implantation and released, similar to, for example, a pen-spring. In this regard, a surgeon or other operator of the device may position the spinous processes in saddle portions 3 of the first and second ends 91, 93, more easily.

In certain embodiment, implant 90 may be secured in position between the spinous processes for example, by one or more screws or pins 97 and/or by one or more straps 98 positioned around one or both spinous processes.

Figure 10:
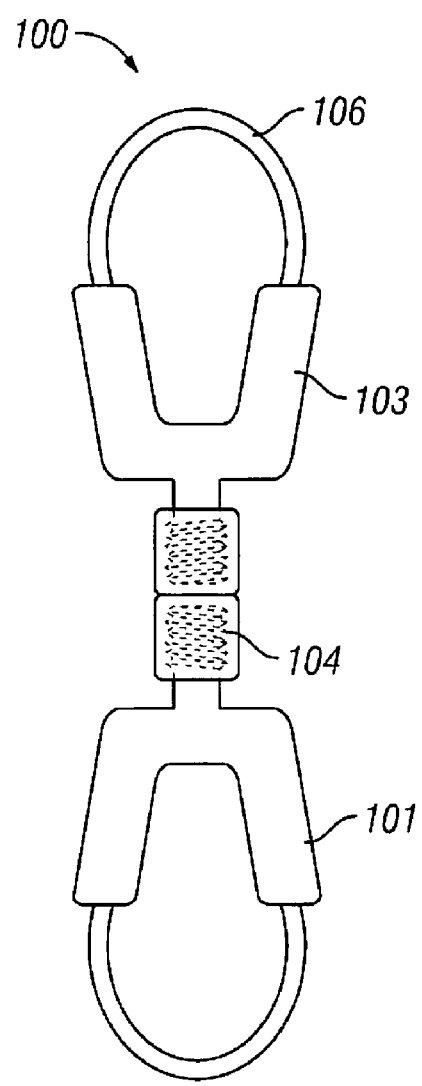
FIG. 10 depicts other embodiments of implants of the invention.

Referring to FIG. 10 another implant 100 according to the invention is shown. Implant 100 generally comprises a first portion 101 and a second portion 103. One or both portions may have a threaded connection or turnbuckle 104 that threadedly connects the first and second portions together. Implant 100 may be expanded or contracted in the cranial-caudal or longitudinal direction by rotating tumbuckle(s) 104. In this regard, implant 100 may be adjusted after implantation between spinal processes, by virtue of the threaded connection between the first and second portions 101, 103, which allow the first and second portions to move further apart and closer together with respect to each other after implant 100 is inserted into the patient. In this regard, implant 100 may be used to distract the adjacent spinous processes in situ without the need for an additional distraction tool. Similar to previous embodiments, implant 100 may be secured in position between the spinous processes for example, by one or more screws or pins and/or by one or more straps 106 that wrap around one or both spinous processes. Both of the first and second portions of implant 100 may be inserted between the spinous processes substantially simultaneously, or one portion may be inserted followed by the other portion.

Figure 11:
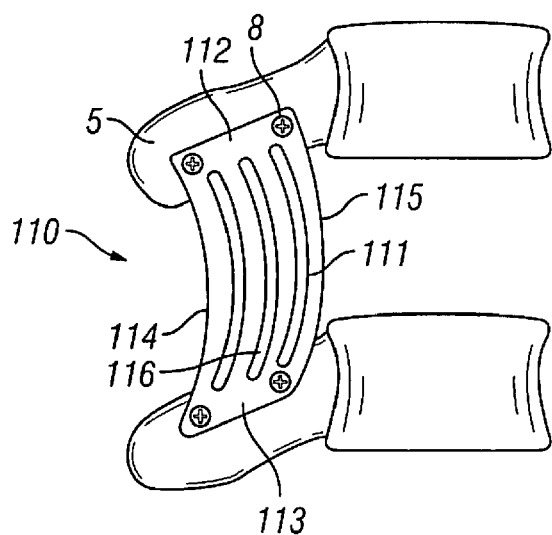
FIG. 11 depicts other embodiments of implants of the invention in relation to the spinal processes between which the implants are implanted.

Referring to FIG. 11, another embodiment of an implant 110 according to the present invention is shown. In general, implant 110 may be resiliently compressible or expandable such that the implant may support and or adjust to dynamic movement of the spine. As seen in FIG. 11, implant 110 is shown in relation to two adjacent spinous processes 5 between which the implant is implanted. Implant 110 generally comprises a main body 111 having at least one top end 112 and at least one bottom end 113, a first posterior side 114 extending between the top and bottom end, and a second anterior side 115 extending from the top end 112 to bottom end 113. At least a portion of each of the first and second sides 114, 115 is curved. In some embodiments, at least one of the first and second sides 114, 115 is curved in a convex direction (e.g. second side 115 in FIG. 11) and at least one of the first and second sides 114, 115 is curved in a concave direction (e.g. the first side 114 in FIG. 11). In operation, the curved configuration may function similar to a biasing member or spring such that implant 110 may be flexible or resiliently compressed or expanded in the cranial-caudal direction. Optionally, the main body 111 may contain one or more openings 116. Opening(s) 116 may optionally be curved similar to the convex and concave directions of the first and second sides 114, 115 of the body as depicted in FIG. 11, and may provide or enhance flexibility of the implant. The material(s) from which the implant is made may also provide or enhance flexibility of the implant. For example, implant 110 may be made from a resiliently deformable material such that the implant may be resiliently compressible or expandable to support and or adjust to dynamic movement of the spine. In this regard, the shape and configuration of the implant may allow the implant to resiliently deform in the cranial-caudal direction and provide dynamic support between the adjacent spinous processes to accommodate extension and flexion of the spine.

Embodiments according to the present invention may be positioned or implanted such that the body 111 is entirely between two spinous processes 5, or as depicted in FIG. 11, one or both of the top 112 and bottom 113 ends of the body may overlap one or more sides of one or more of the spinous processes. In embodiments where one or both of the top and bottom ends overlap to the one or more of the sides of one or more of the spinous processes, the body 111 may have two top ends 112 (one on either side of a spinous process) and two bottom ends 113 (one on either side of a spinous process). Alternatively, the top and bottom ends of the implant may overlap with the spinous processes on the same side, or a second implant may optionally be implanted on the opposite side of the spinous processes. In certain embodiments, implant 110 may be secured in place by the methods described herein, which may include for example, connecting implant 110 to the spinous process through holes 8 in the implant.

Figure 12:
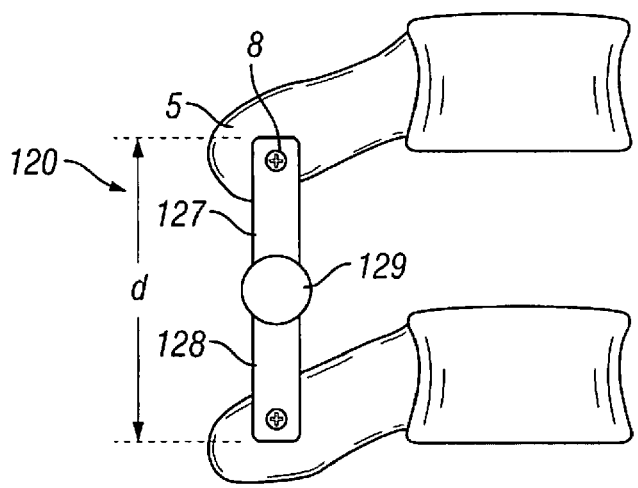
FIG. 12 depicts other embodiments of implants of the invention in relation to the spinal processes between which the implants are implanted.

Referring to FIG. 12, another embodiment of an implant 120 according to the present invention is shown in relation to two adjacent spinous processes 5 between which the implant is implanted. In general, implant 120 may allow dynamic relative movement between adjacent spinous processes. Implant 120 is adapted and configured to be placed between adjacent spinous processes, and generally includes a top body 127 and a bottom body 128 rotatably interconnected at a rotation body 129. The top body and bottom body may be of any formation so long as they can rotate as desired about the rotation body as desired for implantation and/or for flexion purposes after implantation. The rotation body may be for example, a ball and socket configuration. For example, the ball and socket configuration may allow implant 120 adjust to dynamic movement of the spine once the implant is inserted. In this regard, implant 120 may accommodate limited contraction and expansion of adjacent spinous processes in the cranial-caudal direction as well as relative movement in the medial-lateral direction and posterior-anterior direction to accommodate dynamic movement of the spine. In the cranial-caudal direction, implant 120 may have a maximum distraction distance (d) to support limited flexion of the spine.

According to certain embodiments of the present invention one or both of the top and bottom bodies may overlap to the side of the spinous process. According to these embodiments, the top body 127 and/or the bottom body 128 may overlap on either side of a spinous process. Alternatively, the top body 127 and bottom body 128 overlap with the spinous processes on the same side, and a second implant may optionally be implanted on the opposite side of the spinous processes. In other embodiments, implant 120 may include saddle portions as described previously.

According to methods of the present invention, the implant may be inserted between two adjacent spinous processes 5, where the top body 127 and/or the bottom body 128 are rotated about the rotation body 129 (either towards or away from each other), such that the height (d) of the implant is not at its maximum. After the implant is positioned between spinous processes, the top body 127 and/or bottom body 128 may be rotated with respect to the rotation body 129 until the implant is positioned at a desired height (d). The implant may be locked or secured to the desired height or adapted to allow a certain flexibility or rotation about the rotation body 129. In certain embodiments, implant 120 may be secured in place by the methods described herein, which may include for example, connecting implant 120 to the spinous process through holes 8 in the implant.

Figure 13A:
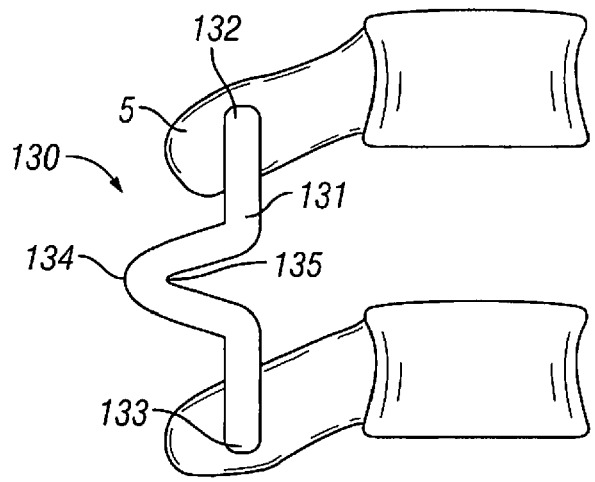
FIGS. 13a-13b depict a side and front view of other embodiments of implants of the invention, where the side view is depicted in relation to the spinous processes between which the implants are implanted.
Figure 13B:
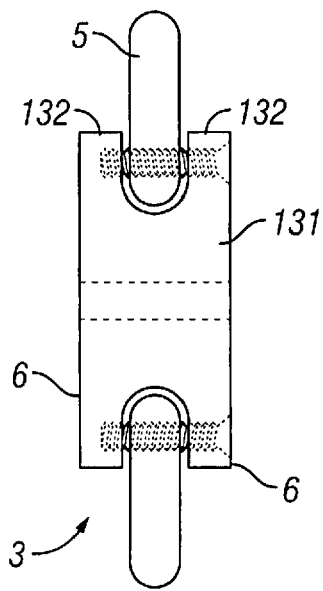

FIGS. 13a-b depict another embodiment of an implant 130 according to the present invention in relation to two adjacent spinous processes 5 between which the implant is implanted. Similar to implant 110 described with respect to FIG. 11, implant 130 may be resiliently compressible or expandable such that the implant may support and or adjust to dynamic movement of the spine. As seen in FIG. 13a, implant 130 generally includes a body 131 having a top end 132 and a bottom end 133, a first side 134 extending between the top and bottom end, and a second side 135 extending from the top to bottom end, where at least a portion of each of the first and second sides are curved. FIG. 13 depicts embodiments where at least one of the first and second sides has a portion curved in a convex direction and at least one of the first and second sides has a portion curved in a concave direction. In operation, the curved configuration may function similar to a biasing member or spring such that implant 130 may be flexible or resiliently compressed or expanded in the cranial-caudal direction. The material(s) from which the implant is made may also provide or enhance flexibility of the implant. For example, implant 130 may be made from a resiliently deformable material such that the implant may be resiliently compressible or expandable to support and or adjust to dynamic movement of the spine. In this regard, the shape and configuration of the implant may allow the implant to resiliently deform in the cranial-caudal direction and provide dynamic support between the adjacent spinous processes to accommodate extension and flexion of the spine.

Embodiments according to the present invention may comprise body 131 positioned entirely between the spinous processes, or as depicted in FIG. 13, one or both of the top 132 and bottom 133 ends of the body 131 may overlap to the side of the spinous process. In embodiments where one or both of the top and bottom ends overlaps to the side of the spinous process body 131 may have saddle portions 3 on the top and bottom ends of implant 130 wherein each saddle includes lateral saddle walls 6 (one on either side of a spinous process). A non-limiting example of such an embodiment is depicted in FIG. 13b, depicting two top saddle walls 6 on either side of a spinous process, and two bottom saddle walls 6 on either side of a spinous process. In an alternative embodiment, the top end 132 and bottom end 133 of implant 130 may overlap the spinous processes on the same side of the spinous process, and a second implant may be optionally implanted on the opposite side of the spinous processes. Implant 130 may be secured in place by any suitable methods described herein.

Figure 14A:
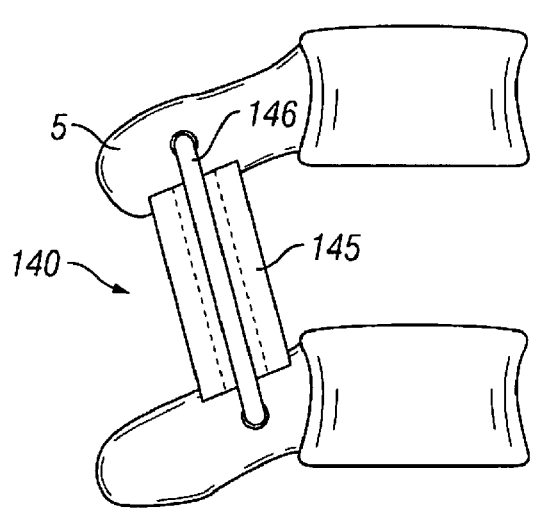
FIGS. 14a-14b depict a side and front view of other embodiments of implants of the invention, where the side view is depicted in relation to the spinal processes between which the implants are implanted.
Figure 14B:
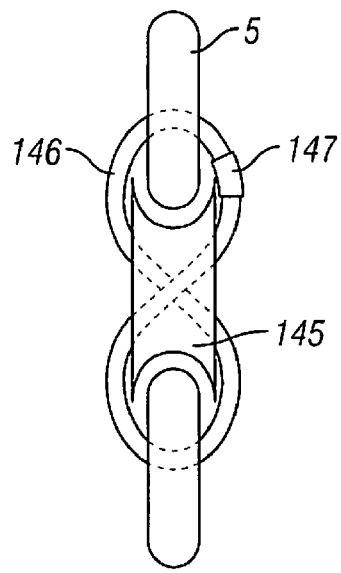

Referring to FIGS. 14a-b, another embodiment of an implant 140 according to the present invention is shown in relation to two adjacent spinous processes 5 between which the implant is implanted. Implant 140 is configured and adapted to be placed between adjacent spinous processes, and generally comprises a body 145 and a securing device 146. The body 145 is positioned between the spinous processes 5. The securing device 146 weaves through both the body 145 and the spinous processes (for example, as depicted in the front view FIG. 14b) to maintain the body's position between the spinous processes. The securing device 146 may have a coupling device 147 to tighten securing device 146 or otherwise add tension to the device to secure implant 140 in position.

The body 145 may be of any desirable shape or size such that it fits between the spinous processes, optionally, with portions thereof overlapping to the sides of the spinous processes (as depicted for example in FIG. 14b). The body needn't contact either spinous process at any particular time, but may allow for space between the spinous process 5 and the body 145. The body 145 may be made of any suitable material, but according to certain embodiments, the body 145 is more rigid than the securing device 146.

The securing device 146 may be in one or more pieces, components, and/or materials. Securing device 146 may pass through the body at one or more positions and through the spinous processes, at one or more positions, so long as the body is generally maintained between the spinous processes.

Figure 15A:
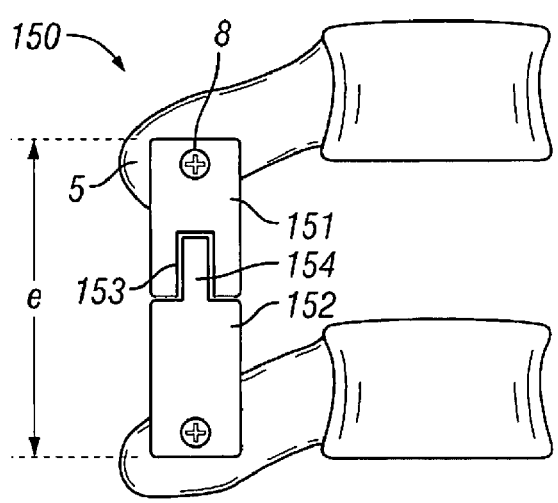
FIGS. 15a-15b depict a side and front view of other embodiments of the invention, where the side view is depicted in relation to the spinal processes between which the implants are implanted.
Figure 15B:
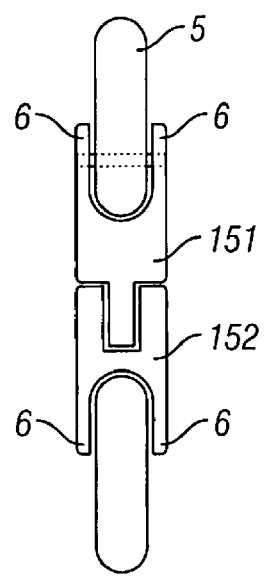

Referring to FIGS. 15*a*-*b*, another embodiment of an implant 150 according to the present invention is shown in relation to two adjacent spinous processes 5 between which the implant is implanted. Implant 150 is configured and adapted to be placed between adjacent spinous processes, and generally comprises a top body 151 and a bottom body 152 rotatably and/or linkingly connected. The top body 151 may have either a male or female fitting portion, and the bottom body 152 may have a corresponding opposite fitting portion. According to one embodiment shown in FIG. 15*a*, the top body 151 has a female fitting portion 153, and the bottom portion has a male fitting portion 154. The fitting portions may be of any configuration so long as they fit together. Similarly, the top body and bottom body may be of any formation so long as they fit together at the male/female portions. The male and female portions may optionally be attached to one another. Further the male and female portions may optionally be attached such that the top portion and bottom portion can rotate as desired about an attachment position for implantation purposes and/or for flexion purposes after implantation. The male and female portions may be for example, a tongue and groove configuration. For example, the tongue and groove configuration may allow implant 150 adjust to dynamic movement of the spine once the implant is inserted. In this regard, implant 150 may accommodate limited contraction and expansion of adjacent spinous processes in the cranial-caudal direction as well as relative movement in the posterior-anterior direction to accommodate dynamic movement of the spine.

According to certain embodiments of the present invention one or both of the top and bottom bodies may overlap to the side of the spinous process as depicted in FIG. 15*a*. According to these embodiments, the top body 151 and/or the bottom body 152 may overlap on both sides of a spinous process (as shown for example, in FIG. 15*b*). In embodiments where one or both of the top and bottom ends overlaps to the side of the spinous process, top and bottom bodies 151, 152 may have saddle portions 3 on the top and bottom ends of implant 150 wherein each saddle portion includes lateral saddle walls 6 (one on either side of a spinous process). A non-limiting example of such an embodiment is depicted in FIG. 15*b*, depicting two top saddle walls 6 on either side of a spinous process, and two bottom saddle walls 6 on either side of a spinous process. In an alternative embodiment, the top end 151 and bottom end 152 of implant 150 may overlap the spinous processes on the same side of the spinous process, and a second implant may be optionally implanted on the opposite side of the spinous processes. Implant 150 may be secured in place by any suitable methods described herein.

Figure 16:
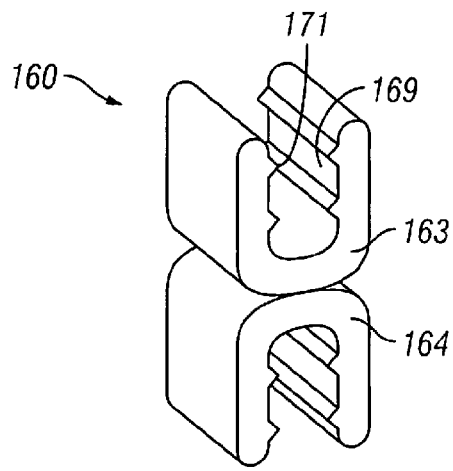
FIGS. 16-18 depict other embodiments of implants of the invention.
Figure 17:
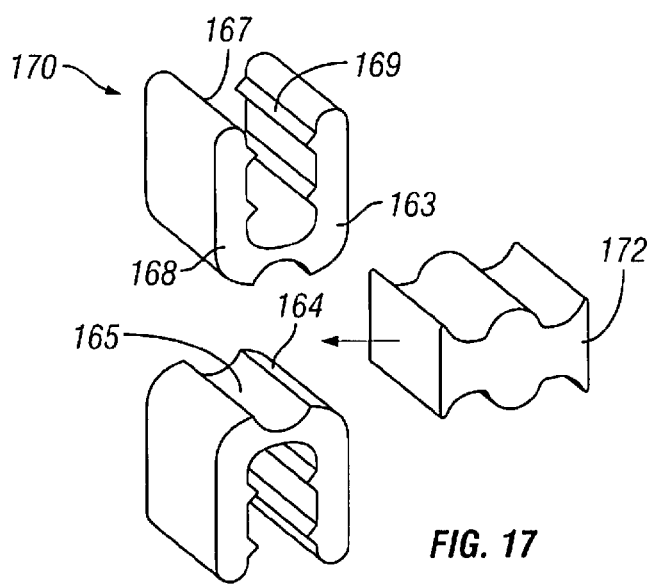
Figure 18:
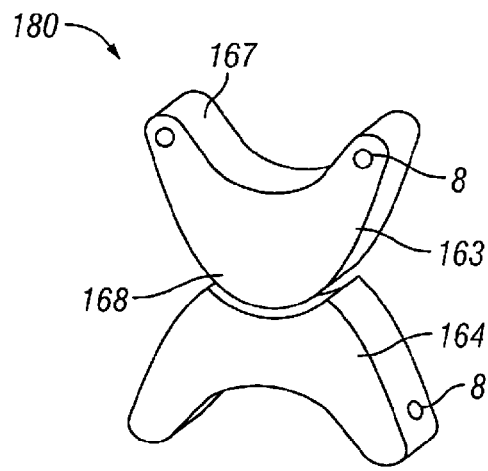

Referring to FIGS. 16-18, additional embodiments of implants 160, 170, 180 according to the present invention are shown. Implants 160, 170, and 180 may allow dynamic relative movement between adjacent spinous processes and generally include a top U-shaped body 163 configured to movingly engage a bottom U-shaped body 164. Each U-shaped body has an open end 167 and a closed end 168. The open ends 167 of the U-shaped bodies are configured such that spinous processes may fit within a space created thereby. The closed ends 168 of the U-shaped bodies are generally configured to be directed toward one another after implantation. The top and bottom U-shaped bodies may be directly or indirectly engaged to one another or they may simply contact one another directly or indirectly. For example, the top and bottom U-shaped bodies may be configured such that the closed ends 168 fit together directly as depicted in FIG. 18 and may include one ore more indented portions 165 to mate or fit with an adjacent U-shaped body. The U-shaped bodies may movingly engage one another similar to a ball and socket configuration. In this regard, implants 160, 170, and 180 may adjust to dynamic movement of the spine once the implant is inserted. For example, the implants may accommodate limited contraction and expansion of adjacent spinous processes in the cranial-caudal direction as well as relative movement in the medial-lateral direction and posterior-anterior direction to accommodate dynamic movement of the spine. In the cranial-caudal direction, the implants may have a minimum distraction distance to support limited extension of the spine.

Indirect contact or attachment may occur for example, in embodiments where there are one or more intermediate bodies, such as intermediate body 172 of FIG. 17. The intermediate body 172 may be of any configuration that fits at least partially between the top and bottom U-shaped portions after insertion of the implant. According to certain embodiments, the intermediate body may be shaped such that it configures to the shape of the top and/or bottom U-shaped bodies. For example, in FIG. 17, the intermediate body 172 is shaped to fit within indented portions 165 provided in the top and bottom U-shaped bodies. The intermediate body 172 may be made of any material suitable for implantation into a mammalian patient and may be selected based on the desired function of the intermediate body. For example, the intermediate body 172 may be made of a polymer material that may be resiliently compressible in the cranial-caudal direction.

Implants in accordance with the present embodiments may be secured in place by the methods described herein, which may include for example, connecting the implant to the spinous process through holes 8 in the implant as depicted for example in FIG. 18. Exemplary implants may be secured to spinous processes, by surface modifications to portions of the implant, such as modifications to surfaces of an inside surface 169 of the U-shaped bodies. Such surface modifications may include mechanical modifications to the surface (see e.g., ridges 171 in FIG. 16) and/or one or more coatings. Such mechanical forces and/or surface modifications may be utilized in addition to, or in place of various other attachment methods described herein.

According to certain methods of the present invention the top U-shaped portion 163 and the bottom U-shaped portion 164 may be inserted between two adjacent spinous processes together or separately. By way of non-limiting example, embodiments such as those depicted in FIG. 16 may be inserted by a straight posterior insertion, or they may be inserted by positioning one U-shaped portion over a spinous process and thereafter rotating the other U-shaped portion over the other spinous process. Any intermediate bodies may be inserted before, substantially simultaneously with, or after insertion of the top and bottom U-shaped portions.

Figure 19:
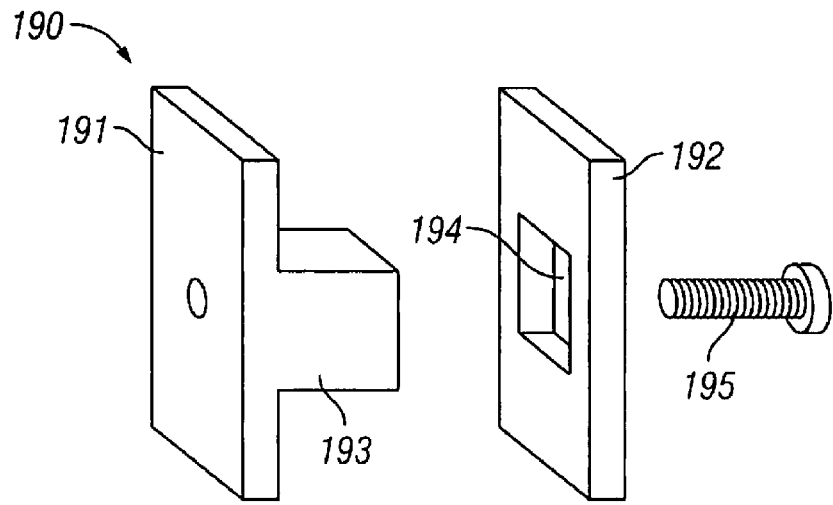
FIGS. 19-21 depict other embodiments of implants of the invention.
Figure 20:
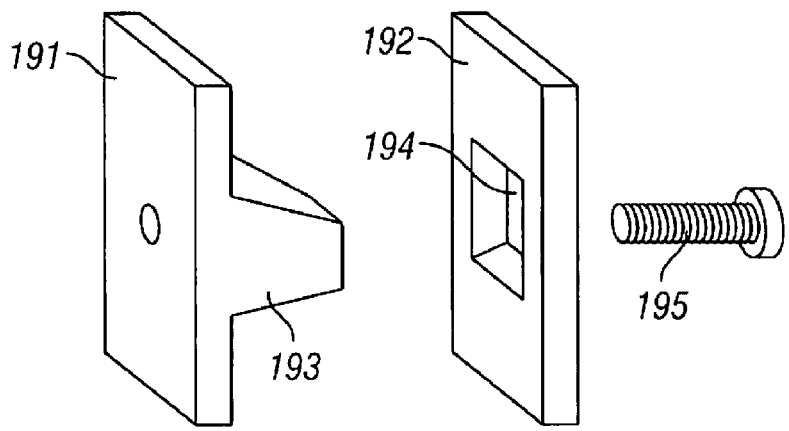
Figure 21:
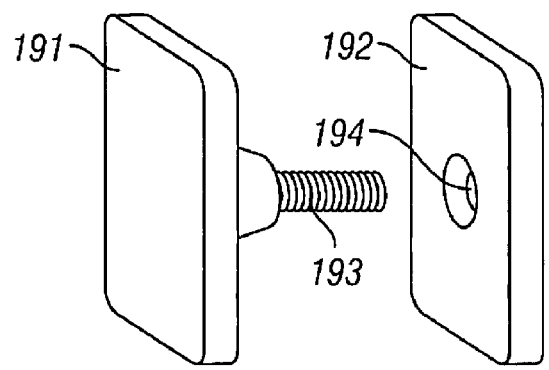

Referring to FIGS. 19-21, additional embodiments of the invention for creating, increasing, or maintaining distraction between adjacent spinous processes are shown. Implants 190, 200, and 210 depicted in FIGS. 19-21 generally include a first body 191 having a male portion 193 and a second body 192 having a female portion 194, wherein the male portion fits partially within the female portion. Upon inserting the male portion into the female portion, spaces are created above and below portions of the male portion that are not within the female portion. Adjacent spinous processes may fit within those spaces and a minimum distraction distance or space may be provided by the male portion.

The male portion 193 may be part of the first body 191 (as depicted in FIG. 19) or it may be one or more portions attached to the first body 191 (as depicted in FIG. 21). The male portion 193 may be curved or tapered as depicted in FIG. 20 such that the further it is inserted into the female portion, the greater the distraction between spinous processes.

Methods of the present invention may include the following: inserting a first body 191 and a second body 192 of the implant on either side of two adjacent spinous processes; fitting the bodies together by inserting a male portion 193 of the first body 191 into a female portion 194 of the second body 192; and adjusting a depth of insertion to a desired depth depending for example, on the size of spinous processes, and/or the desired amount of distraction between the spinous processes. Methods of the present invention may further include securing the implant between adjacent spinous processes.

Implants in accordance with the present embodiments may be secured by the methods described herein. According to certain embodiments, the first body 191 and the second body 192 may be attached to one another, for example, by a pin 195, screw or other fastening device after insertion into a patient to secure the implant in position. Other fastening devices or methods may be used in place of or in addition to attaching the first body 191 to the second body 192 for example, by connecting the implant to one or both spinous processes or other portion(s) of the spine.

Figure 22:
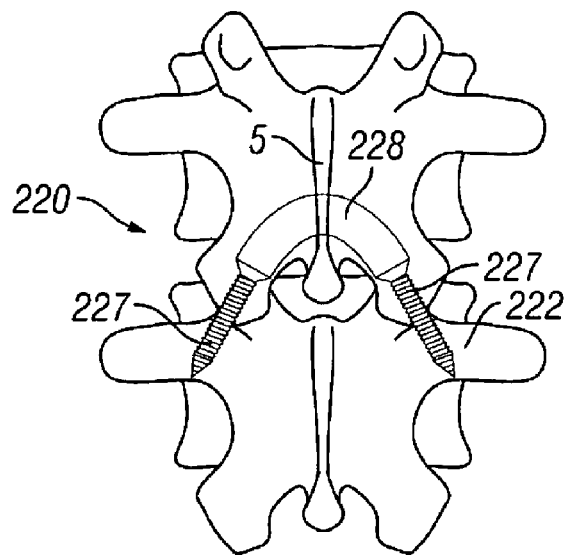
FIGS. 22-24 depict embodiments of the present invention in which the implants are attached to portions of the spine other than a spinous process.
Figure 23:
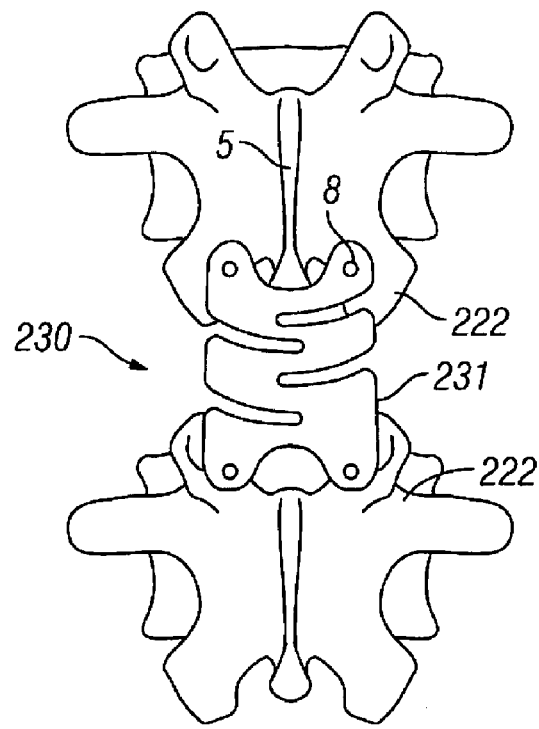
Figure 24:
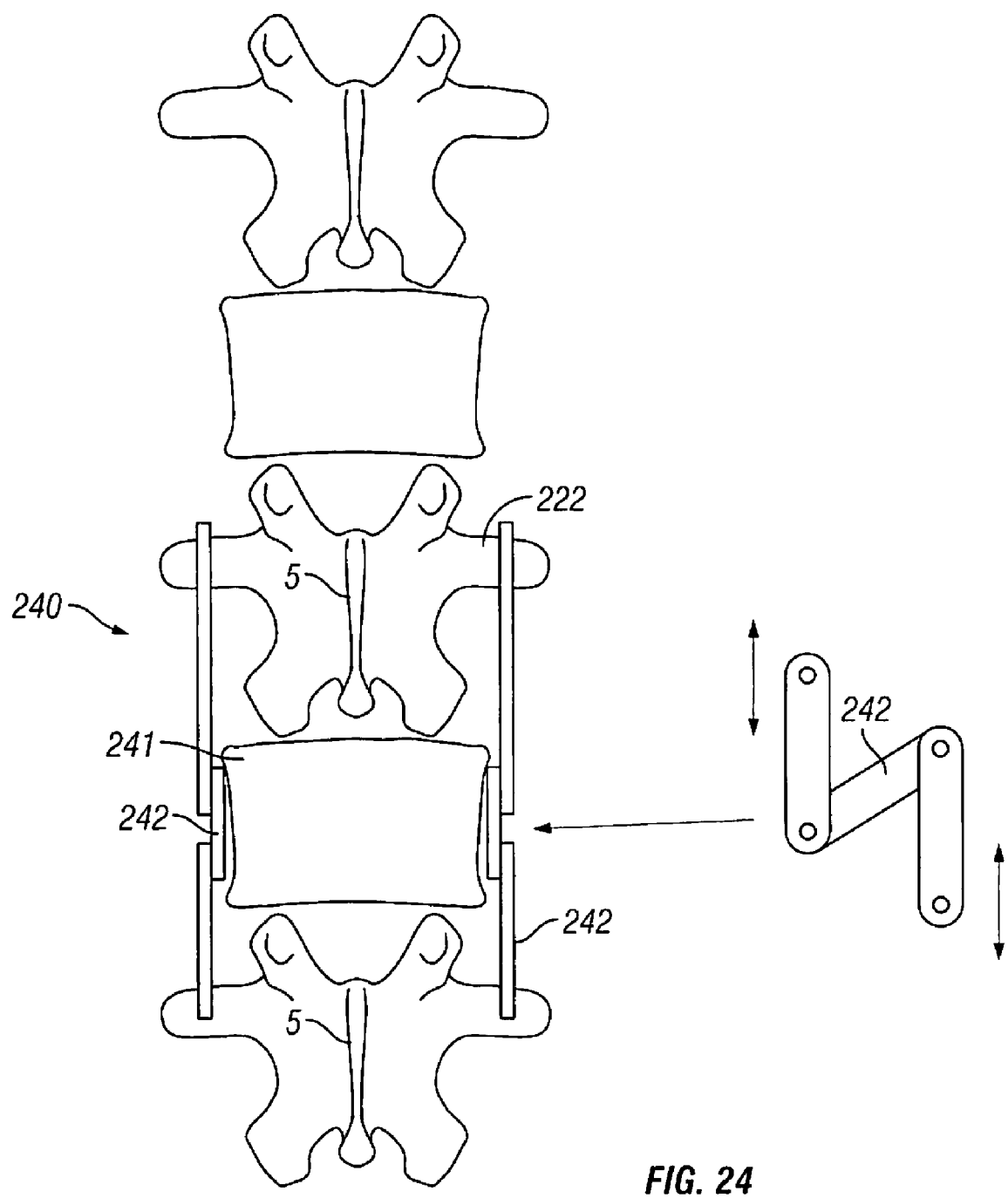

Referring to FIGS. 22-24 additional embodiments of the invention for creating, increasing, or maintaining distraction between adjacent spinous processes are shown, wherein the implants are not directly attached to either spinous process, but are attached to other portions of the spine 222.

As shown in FIG. 22, one embodiment of an implant 220 may include at least two stabilization devices 227, which attach to a portion of the spine 222 and a distraction device 228, which maintains a spinous process 5 in a desired position or range of positions with respect to the portions of the spine to which the stabilization devices 227 are attached. In one embodiment, distraction device 228 is an arcuate member that extends between the stabilization devices 227 and is configured to engage a portion of an adjacent spinous process. The stabilization devices 227 may be for example, screws. The distraction device 228 may be for example, a polymer material and may be more flexible or resilient than the stabilization devices 227. In general, implant 220 may allow dynamic relative movement between adjacent spinous processes. In operation, the curved configuration may function similar to a biasing member or spring such that implant 220 may be flexible or resiliently compressed in the cranial-caudal direction to support and or adjust to dynamic movement of the spine. In this regard, the shape and configuration of the implant may allow the implant to resiliently deform in the cranial-caudal direction and provide dynamic support between the adjacent spinous processes to accommodate extension and flexion of the spine.

As shown in FIG. 23, one embodiment of an implant 230 may be attached to at least two non-spinous process portions of the spine 222. Implant 230 generally comprises a zig-zag-shaped configuration, but embodiments according to the present invention are not limited to such configurations. Embodiments may include any formation and/or be made of any material that provides a desired shape and degree of flexibility. In alternate embodiments, implants may be configured such that they do or do not contact one or both spinous processes upon insertion. Implant 230 may contact one or both spinous processes after insertion based on movement of the patient and/or movement of the spine. In operation, the zig-zag or curved configuration may function similar to a biasing member or spring such that implant 230 may be flexible or resiliently compressed or expanded in the cranial-caudal direction. The material(s) from which the implant is made may also provide or enhance flexibility of the implant. For example, implant 230 may be made from a resiliently deformable material such that the implant may be resiliently compressible or expandable to support and or adjust to dynamic movement of the spine. In this regard, the shape and configuration of the implant may allow the implant to resiliently deform in the cranial-caudal direction and provide dynamic support between the adjacent spinous processes to accommodate extension and flexion of the spine.

As shown in FIG. 24 one embodiment of an implant 240 generally comprises a main body 241 attached to at least one attachment device 242. The attachment device 242 may be attached to at least two non-spinous process portions of the spine 222. In one variation of the embodiment depicted in FIG. 24, attachment devices 242 may have a folding configuration, which may assist in insertion and/or in flexibility or movement of the implant 240 after insertion.

Implant bodies 241 may be in any configuration. According to certain embodiments, implant body 241 may include rigid material(s) and the attachment device 242 may be either rigid or at least partially flexible or maneuverable. In certain embodiments, implant body 241 may be configured such that it may or may not contact one or both spinous processes upon insertion. For example, in certain variations, implant body 241 may contact one or both spinous processes after insertion based on movement of the patient and/or movement of the spine.

Figure 25:
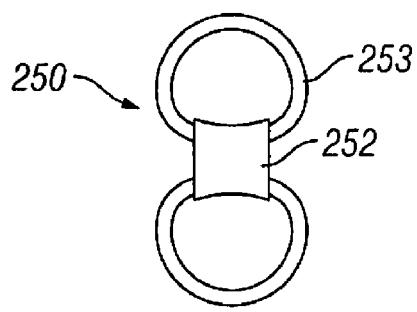
FIGS. 25-26 depict other embodiments of implants of the invention.
Figure 26:
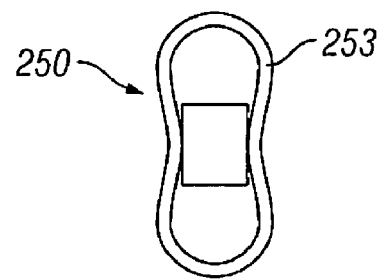

Referring to FIGS. 25-26, additional embodiments of implants according to the invention are shown for creating, increasing, or maintaining distraction between adjacent spinous processes. Implants 250 generally include a body 252 and one or more straps 253. The strap(s) 253 are configured such that they wrap around one or both spinous processes, and can maintain the position of the body 252 with respect to the spinous processes. Maintaining the position of the body 252 with respect to the spinous processes, does not require that the body not move at all, but rather means that the body does not move so far away from between the spinous processes that it does not perform the function of maintaining a distraction between the spinous processes.

Figure 27A:
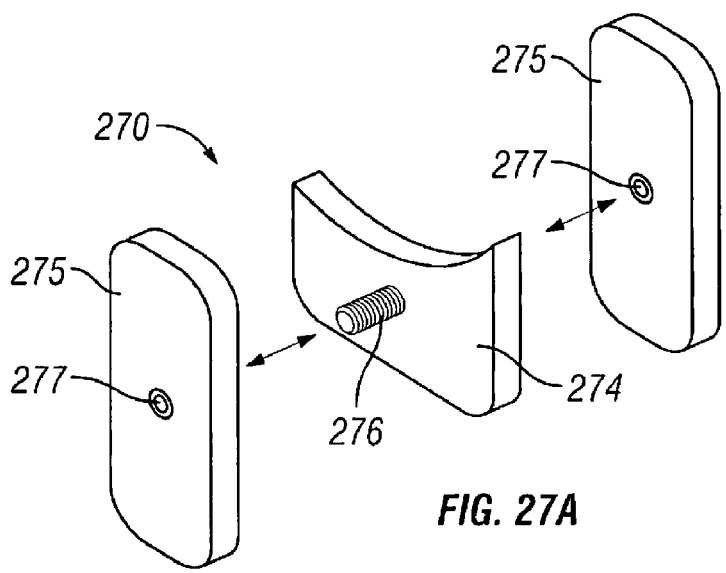
FIG. 27a depicts other embodiments of implants of the invention.
Figure 27B:
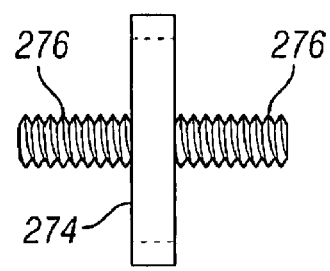

Referring to FIGS. 27a-b, another embodiment of an implant 270 according to the invention is shown for creating, increasing, or maintaining distraction between adjacent spinous processes. Implant 270 generally comprises a center body 274 having at least two male portions 276, and at least two outside bodies 275 having at least two female portions 277. The male and female portions fit together to define a top space above the center body 274, and a bottom space below the center body 274. Two adjacent spinous processes fit within the top and bottom spaces. The center and outside bodies, and the male and female portions may be of any configuration that defines adequate top and bottom spaces in which to fit the spinous processes. According to certain embodiments, the center body 274 is made of a softer material than the outside bodies 275.

As shown in FIG. 27b, the male portions 276 may be ribbed. Ribbing may assist in maintaining the male portions 276 within the female portions 277.

Methods of the present invention may include the following: inserting a center body 274 between two adjacent spinous processes and inserting at least two outside bodies on either side of the adjacent spinous processes; fitting the bodies together by inserting the male portions 276 of the center body 274 into the female portions 277 of the outside bodies 275; and adjusting a depth of insertion of the male portions into the female portions to a desired depth depending for example, on the size of spinous processes, and/or the desired amount of distraction between the spinous processes. Methods of the present invention may further include securing the implant between adjacent spinous processes.

Implants in accordance with the present embodiments may be secured by the methods described herein. According to certain embodiments, the center body 274 and one or both of the outside bodies 275 may be attached to one another, for example, by a pin, screw or other fastening device after insertion into a patient to secure the implant in position. Other fastening devices or methods may be used in place of or in addition to attaching the center body 274 to one or both outside bodies 275, for example, by connecting the implant to one or both spinous processes or other portion(s) of the spine.

Referring to FIGS. 28-33, another embodiment of an implant 300 according to the present invention is shown for creating, increasing, or maintaining distraction between adjacent spinous processes. Implant 300 is adapted and configured to be placed between adjacent spinous processes. As shown in FIG. 28, implant 300 is generally H-shaped or anvil shaped with a saddle portion or central support portion 302 extending laterally along axis 303 between lateral end portions 304, 306. Support portion 302 comprises a top or proximal support surface 308 and a bottom or distal support surface 310 spaced longitudinally apart by a height or distance 312, which generally corresponds to the desired or predetermined distance for distraction or spacing of two adjacent spinous processes. As best seen on FIG. 28, in one embodiment, end portions 304, 306 partially protrude beyond the front and back surfaces 309, 311 of support portion 302 thereby creating a slight indentation along the front and back or anterior and posterior of central portion 302. As described in more detail below, when implant 300 is inserted laterally between adjacent spinous processes, the processes are initially dilated a distance slightly greater than the depth 314 of central portion 302. In this regard, in a first implantation position the spinous processes settle or center adjacent the indented region of central support portion 302, as shown for example in FIG. 40. In addition, when implant 300 is in a second implantation position, as shown in FIGS. 41-42, the indentations on the front and back are configured and dimensioned to avoid contact with the dura.

End portions 304, 306 extend generally perpendicular to support portion 302 and generally extend longitudinally beyond support surfaces 308, 310 and generally form wing-like structures on the lateral ends of implant 300. End portion 304 extends longitudinally along axis 305 and end portion 306 extends longitudinally along axis 307. In one embodiment, axes 305 and 307 are generally perpendicular to axis 303. In another embodiment, axes 303, 305, and 307 are coplanar. End portions 304, 306 are spaced laterally apart by a width distance 315, which generally corresponds to the desired or predetermined distance for accommodating the width of the spinous processes. The inner surfaces or walls of end portions 304, 306 may contact or engage the lateral sides of the spinous processes when the implant is implanted. In this regard, end portions 304, 306 are configured and dimensioned to generally prevent or limit lateral movement of the implant when the implant is implanted. In one variation, the space between end portions 304, 306 may be angled toward the center of implant to align the spinous processes with respect to central portion 302. According to one aspect of the present invention, multiple implants of varying widths 315 may be provided in a kit for appropriate selection and installation by a surgeon.

In one embodiment, end portion 304 generally comprises a cylindrical, bullet, anvil or horn shape extending longitudinally from a rounded bottom or distal end 316 to a narrower tip, nipple, or bull nose shaped top or proximal end 318. As best seen when viewed from the front as in FIG. 29, in one embodiment, the outer lateral surface portion 320 of end portion 304 is curved laterally outward from bottom end 316 to a point adjacent top end 318. In this regard, the curved aspect resembles a horn or boot and facilitates a combined lateral and rotational or pivotal insertion between spinous processes as the curved profile provides clearance during in-situ rotation or pivoting about an axis extending in the anterior-posterior direction through end portion 304 adjacent the bottom end 316. In operation, implant 300 may be pivoted about bottom end 316 during lateral insertion such that end portion 304 is rotated from a lateral or horizontal position (shown in FIG. 39) to an upright or longitudinal position (shown in FIG. 40). According to another aspect of an embodiment of the invention, a rounded or curved inner transition 322 may be provided between inner lateral surface 324 of end portion 304 and proximal support surface 308 of support portion 302. Referring to FIG. 33, in one embodiment end portion 304 may be tapered or increase in thickness along its length such that the proximal tip 318 is narrower or thinner than the base or bottom end 316 when viewed from the end. At its thickest point, front surface portion 323 of end 304 is spaced from back surface portion 325 of end 304 by a distance 327. In this regard, the tapered feature acts or performs in a cam-like manner to translate the lateral or pivotal force to separate the spinous processes in the longitudinal or cranial-caudal direction as the implant is inserted. In alternate embodiments, outer lateral surface or portion 320 of end portion 304 may have differing shapes or curves that may facilitate lateral and/or pivotal insertion and/or provide additional mechanical advantage to distract the spinous processes in operation.

Referring to FIG. 30, in one variation, support portion 302 has a generally rectangular cross-section with a height 312 and a depth 314. In one embodiment, height 312 is greater than depth 314. In one variation, height 312 is about 2 mm greater than depth 314. In alternate embodiments, any suitable range of heights and depths may be utilized. In one embodiment, a center locating pin 326 may be positioned in the center of central portion 302 extending in a longitudinal direction and a lateral end locating pin 329, best seen in FIGS. 29 and 31, may extend perpendicular to axis 303 in an anterior-posterior direction to facilitate the location of implant 300 using fluoroscopic devices known to those skilled in the art. Locating pins 326, 329 may be made from any known radio-opaque material known to those skilled in the art, including, but not limited to, tantalum.

As best seen in FIGS. 29 and 32, lateral end portion 306 generally comprises a thin wall or plate having a uniform thickness 328. As shown in FIG. 32, when viewed from the end, end portion 306 has a generally arcuate, bent, or teardrop shaped top or proximal end 330 and a rounded bottom or distal end 332 and a hexagonal opening 333 to accommodate or engage an insertion tool 424 (shown in FIGS. 39-41 and 50-52). In alternate embodiments, any suitable attachment means known to those skilled in the art may be utilized to engage insertion tool 424 with implant 300, including, but not limited to, a threaded engagement. In one embodiment, opening 333 may extend through the entire body of the implant, creating a cannulated body. The arcuate proximal end 330 is configured and dimensioned to accommodate positioning between spinous processes such that the anterior cutout or inner curve 334 of end 330 is shaped and sized to contact the lamina upon installation. Anterior curve 334 in end portion 306 facilitates anterior positioning as it allows implant 300 to wrap around, accommodate or engage the lamina upon installation in an anterior position with respect to the spinous processes. In another embodiment, a similar sized and shaped anatomical anterior cutout may be provided on first end portion 304. According to one embodiment, implant 300 is configured to be positioned in a final installation location anterior the spinous processes. In this regard, in one embodiment implant 300 may be maintained or held in the installed position without additional fixation devices. As best seen in FIG. 29, distal end 332 protrudes longitudinally beyond distal support surface 310 in the distal direction. In one variation, the protruding distal end 332 of second end portion 306 is configured to prevent over-insertion or over rotation of implant 300 when the implant is positioned into the first installation position. In one embodiment, a transition, ramp, or chamfer 336 is provided between end portion 306 and support portion 302. In another variation chamfer 336 comprises a generally linear transition or pyramid-like step or increase from support portion 302 to end portion 306. In general, chamfer 336 functions as a ramp or transition to facilitate positioning or centering of the spinous process adjacent support surfaces 308, 310.

In certain variations of the aforementioned embodiment, implant 300 may be attached to one or both of the adjacent spinous processes to secure the implant. By way of non-limiting example, the implant may have one or more openings 335 which permit the attachment of the implant to one or both spinous processes by one or more fastening devices, such as, for example, a suture or screw. In another embodiment, one or more additional openings may be provided on the opposite end portion to accommodate a fixation or fastening device.

In one embodiment, at least a portion of the front and back surfaces comprise textured, striated, or grooved portion(s) 337. In this embodiment, portions 337 comprise multiple lateral grooves 339 extending laterally along a portion of the front and back surfaces of end portions 304, 306. In operation, grooved portions 337 may prevent movement of implant 300 in any non-parallel direction with respect to any portion of the spinous processes that it may contact upon implantation. In this regard, groove portions 337 facilitate mechanical fixation with respect to the spinous processes.

Figure 34:
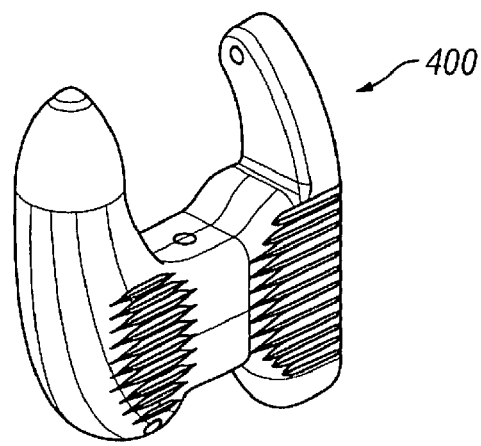
FIG. 34 is a perspective view of another embodiment of an implant according to the present invention.
Figure 35:
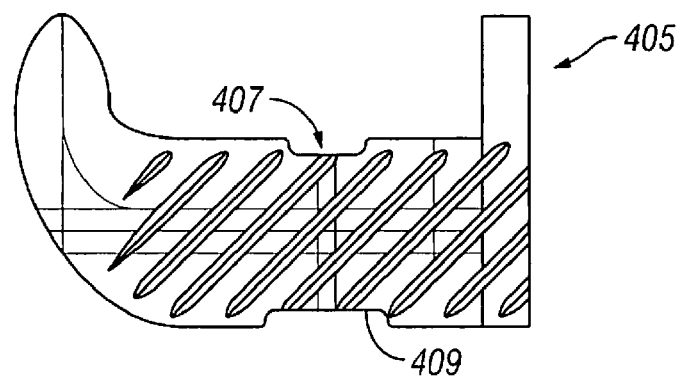
FIG. 35 is a front view of the implant of FIG. 34.
Figure 36:
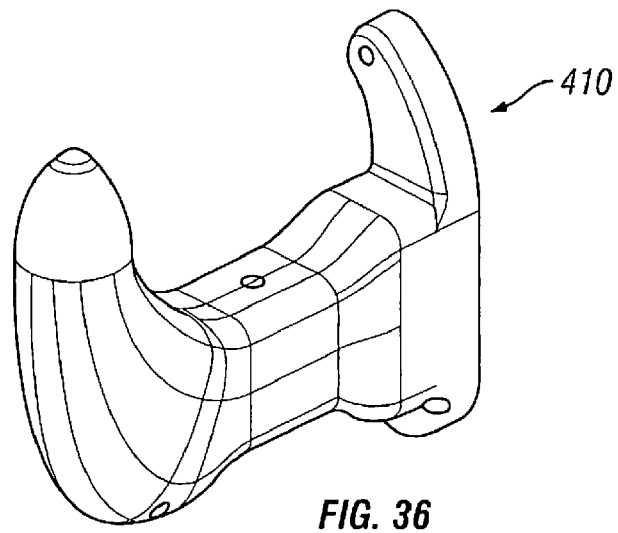
FIG. 36 is a perspective view of another embodiment of an implant according to the present invention.

FIGS. 34-36 depict alternate implants 400, 405, 410 according to the present invention adapted to be placed between adjacent spinous processes. Implants 400, 405, 410 are similar to implant 300 of FIGS. 28-33, except that the amount of lateral grooves may be more or less than lateral grooves 339 of implant 300. Referring to FIG. 34, in one embodiment, implant 400 may comprise more grooves and as shown in FIG. 36, in another embodiment, implant 410 may be free from grooves altogether. Referring to FIG. 35, according to one embodiment, implant 405 may comprise grooves along a majority of the front and back surfaces and may be positioned at an angle. According to another aspect of the invention, implant 405 may comprise indented regions 407, 409 along the central support portion to accommodate or center a portion of the spinous processes therein. In one variation, proximal indented region 407 may have a different width than distal indented region 409. In this regard, the differing widths may accommodate differing contact widths of adjacent processes on the posterior and distal sides upon implantation. According to one aspect of the present invention, multiple implants of varying groove arrangements may be provided in a kit for appropriate selection and installation by a surgeon.

Figure 37:
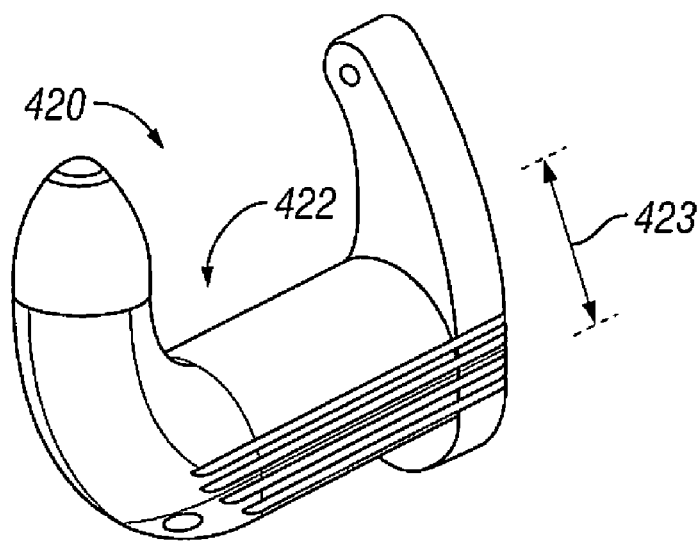
FIG. 37 is a perspective view of another embodiment of an implant according to the present invention.
Figure 38:
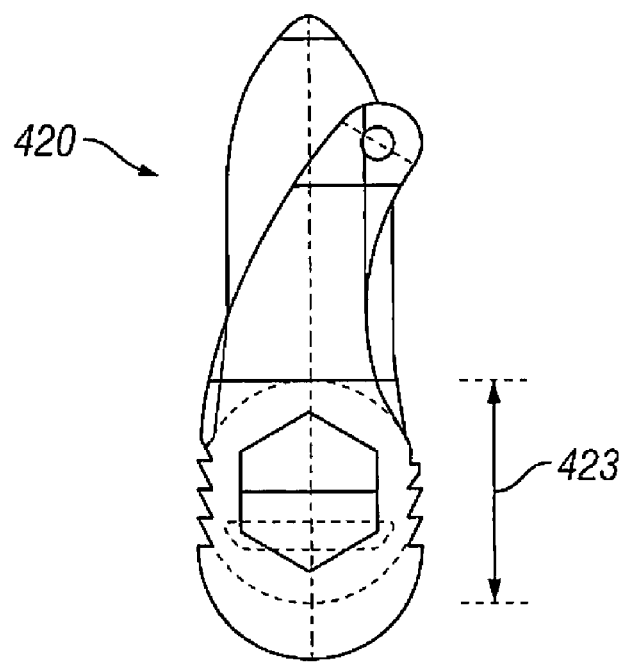
FIG. 38 is an end view of the implant of FIG. 37.

Referring to FIGS. 37-38, another implant 420 according to the present invention is shown. Implant 420 is similar to implant 300 described above, except that central portion 422 has a circular cross-section with a generally constant diameter 423 along its lateral axis. In operation, diameter 423 provides a constant distraction distance and once the implant is implanted and after the spinous processes are positioned adjacent central portion 422 of the implant 420, the implant may maintain the spinous processes in a distracted or spaced condition, for example where the distraction distance or diameter 423 of implant 420 is greater than a pre-implantation distance between the spinous processes. According to one aspect of the present invention, multiple implants having varying cross-sectional shapes and sizes may be provided in a kit for appropriate selection and installation by a surgeon. For example, in certain kits according to the invention, implants may be provided with heights ranging from about 8 mm to about 16 mm in 1 mm increments, and widths ranging from about 12 mm to about 20 mm in 1 mm increments. In some kits according to the invention, implants may be provided having a depth from about 6 mm to about 14 mm.

Figure 39:
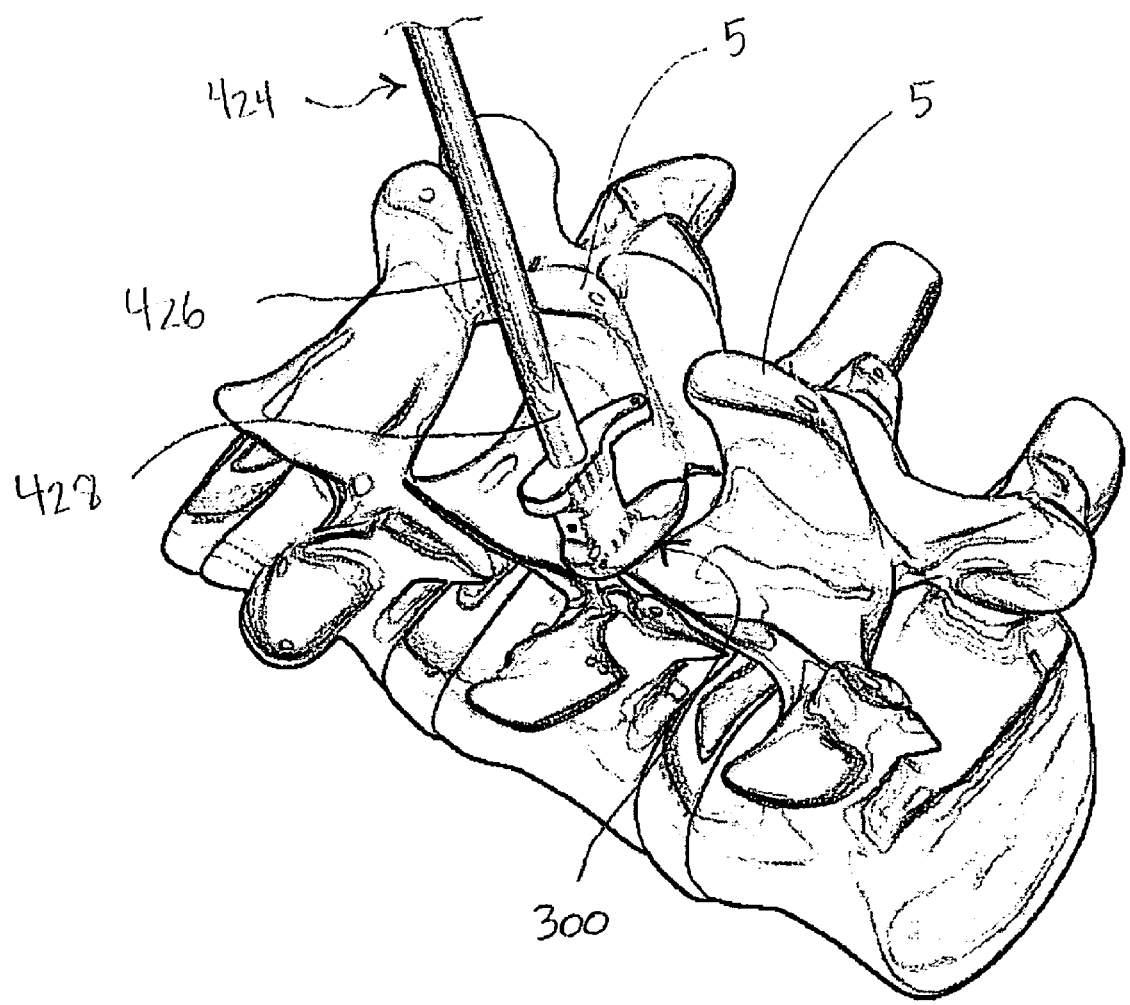
FIGS. 39-42 are perspective views demonstrating steps according to one embodiment of a method of installation of the implant of FIGS. 28-32.
Figure 40:
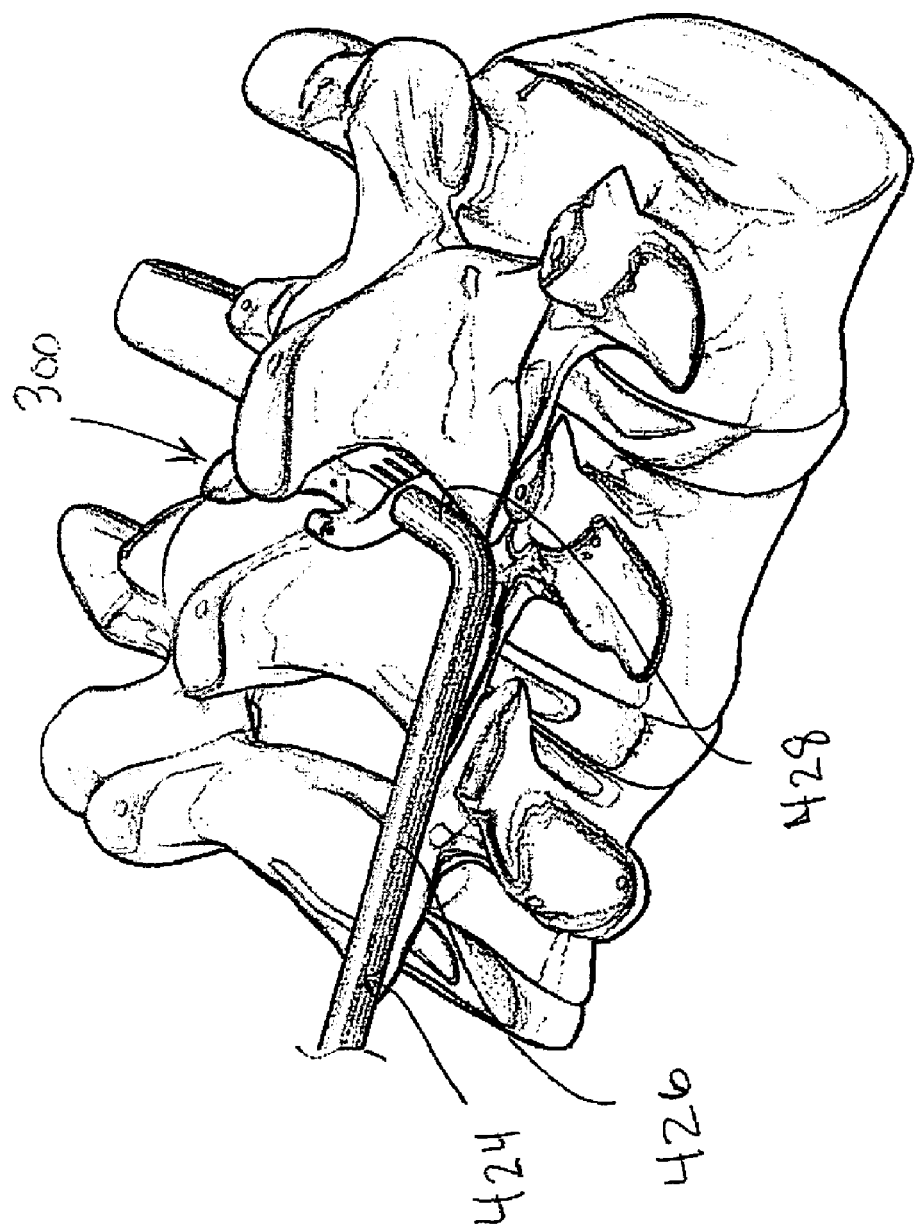
Figure 41:
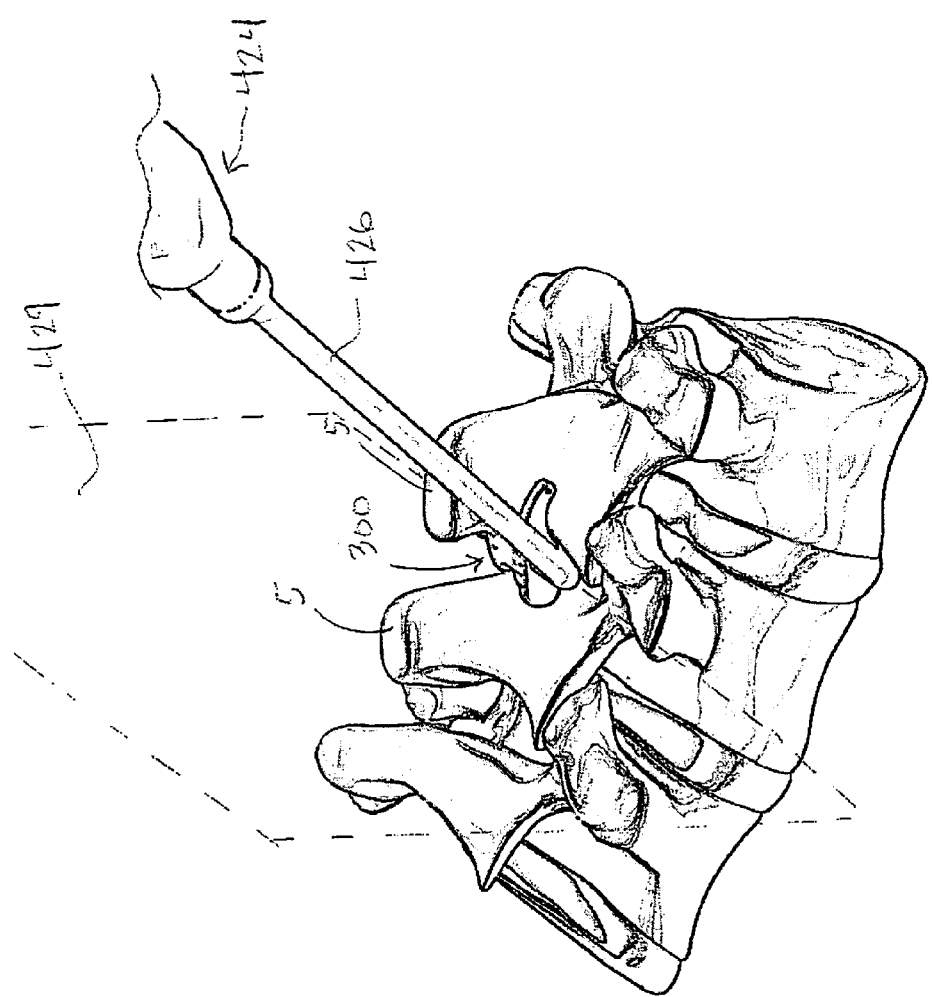
Figure 42:
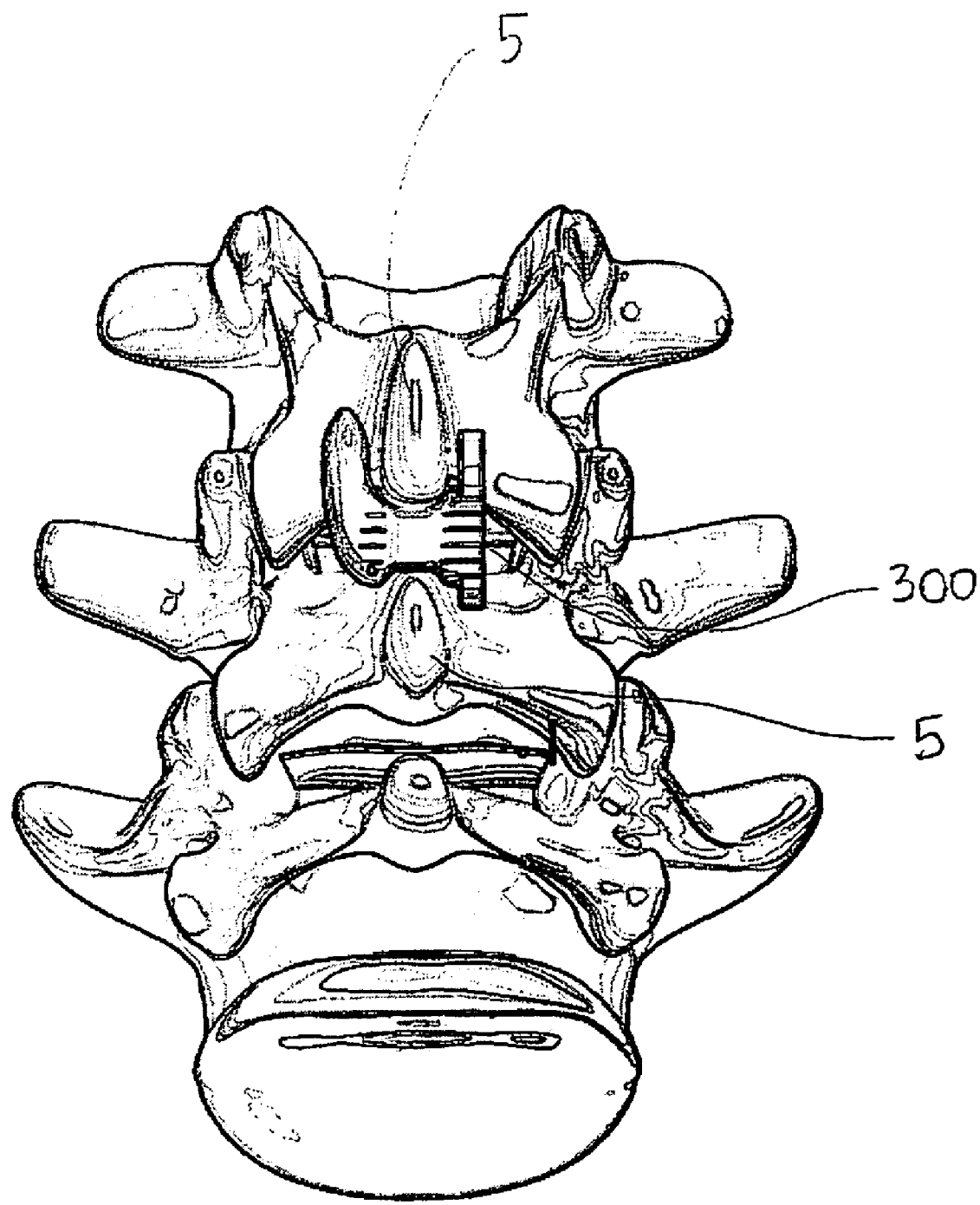
Figure 51:
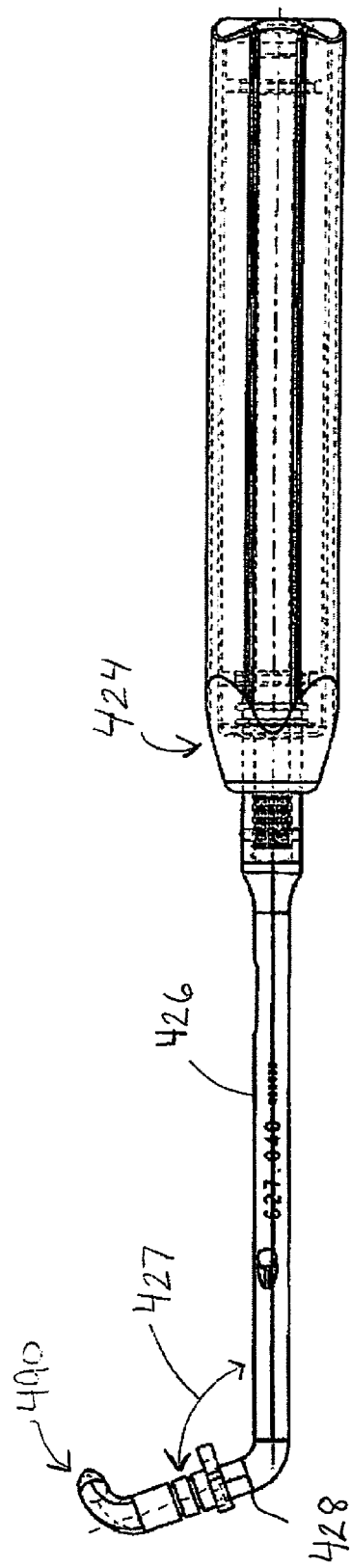
Figure 52:
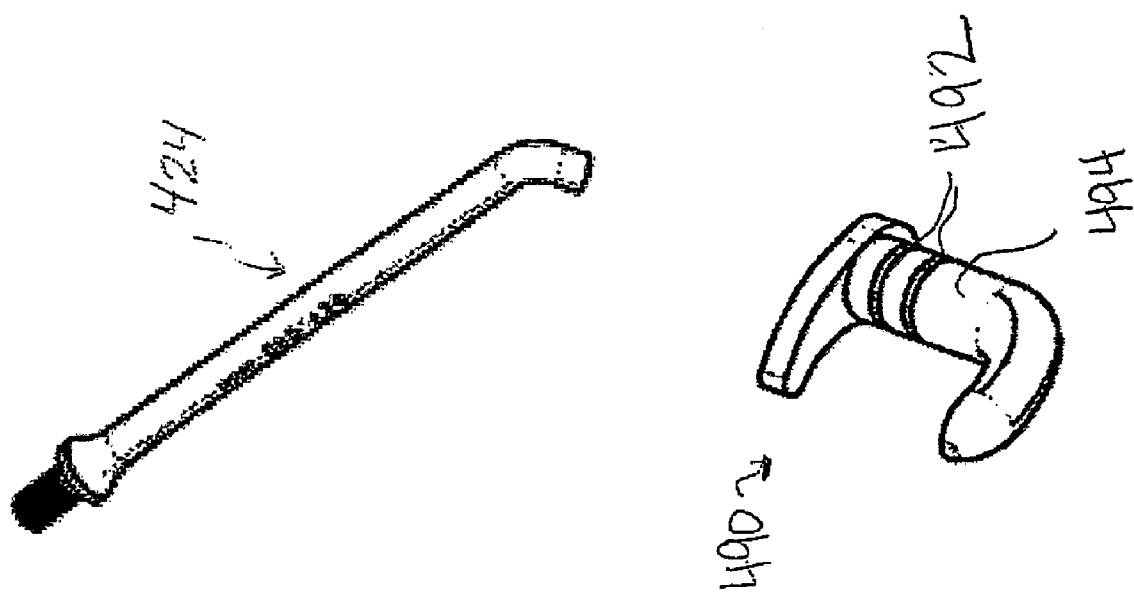

Referring to FIGS. 39-42 and 50-52, according to methods of the present invention, implants 300, 400, 410, 420 may be inserted between two adjacent spinous processes 5 using an insertion tool 424. In one embodiment, as best seen in FIG. 51, insertion tool 424 comprises a shaft 426 with a tip 428 extending generally at an angle 427 with respect to shaft 426. In one variation, angle 427 may be between about 100 and 135 degrees. As explained above, in one variation, tip 428 comprises a hexagonal perimeter sized and shaped to engage a similarly shaped opening on the implant, such as opening 333 shown in FIG. 32. In alternate embodiments, any suitable attachment means known to those skilled in the art may be utilized to engage insertion tool 424 with implant 300, including, but not limited to, a threaded engagement. In one embodiment of a method according to the invention, as shown for example in FIG. 39 for implant 300, a portion of end portion 304 may contact at least one of the adjacent spinous processes. In one variation, the implant may be inserted laterally such that the bull nose tip or distal end 318 of end portion 304 is inserted between adjacent spinous process and the implant may be laterally advanced and pivoted to dilate or distract the processes until the implant is positioned into or adjacent the saddle or support portion 302 of the implant, as shown in FIG. 40. As shown in FIG. 40, the adjacent spinous processes may contact or engage front and back surfaces 309, 311 of support portion 302. Subsequently, in another embodiment, implant 300 may be rotated 90 degrees to further distract the spinous process until the two adjacent spinous processes engage or contact the top and bottom support surfaces 308, 310, as shown in FIG. 41. After insertion tool 424 is removed, implant 300 is positioned in a final implantation position as shown in FIG. 42.

As explained above with respect to other embodiments, in this embodiment the implant itself may serve to dilate or distract the spinous processes as it is being inserted and/or after insertion. For example, the implant may be initially inserted laterally and pivotally between the compressed adjacent spinous processes as shown in FIG. 39. In one embodiment, the supraspinous ligament need not be removed. In operation, lateral end portion 304 of implant 300, engages the adjacent spinous processes as the implant is inserted laterally and pivoted to act or perform in a cam-like manner to translate the lateral/pivotal force to separate the spinous processes in the longitudinal or cranial-caudal direction as the implant is inserted. For example, in an initial pre-implantation condition, the adjacent spinous processes may be in an initial compressed state such that the initial space or longitudinal distance between the processes may be equal to or smaller than distance 312 of implant 300. During lateral and pivotal insertion of implant 300, as shown in FIG. 39, proximal tip 318 of lateral end portion 304 of the implant may contact one or both of the spinous processes 5 and may initially distract the processes. As the implant is inserted further between the spinous processes and pivoted, as explained above, the tapered surface portions 323, 325 may distract the spinous processes further apart from one another, until the implant is positioned into a first implantation position (FIG. 40) and the spinous processes are fitted adjacent the front and back surfaces 309, 311 of saddle or support portion 302 of the implant. In one embodiment, implant 300 may be rotated about 90 degrees about the lateral axis 303 from the horizontal or lateral position shown in FIG. 40 to the vertical or longitudinal position shown in FIG. 41 and the spinous processes are fitted into the upper and lower surfaces of saddle or support portion 302 of the implant separated by distraction distance 312. In this regard, in one embodiment, shaft 426 of insertion tool 424 is generally movable within the realm of the incision created between about 45 degrees on both sides of a lateral plane 429. After insertion tool 424 is removed, implant 300 is positioned in a final implantation position as shown in FIG. 42. Once the implant is implanted and after the spinous processes 5 are fitted into the saddle or support portion 302 of implant 300, the implant may maintain the spinous processes in a distracted or spaced condition, for example where the distance 312 of the implant is greater than a pre-implantation distance between the spinous processes.

Figure 43:
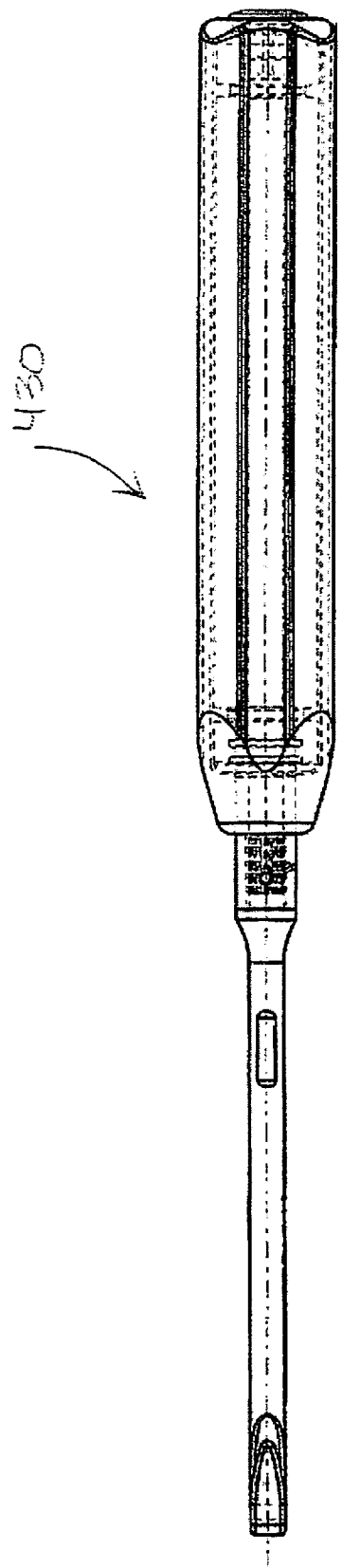
FIGS. 43-44 depict one embodiment of a muscle distraction tool constructed in accordance with the present invention.
Figure 44:
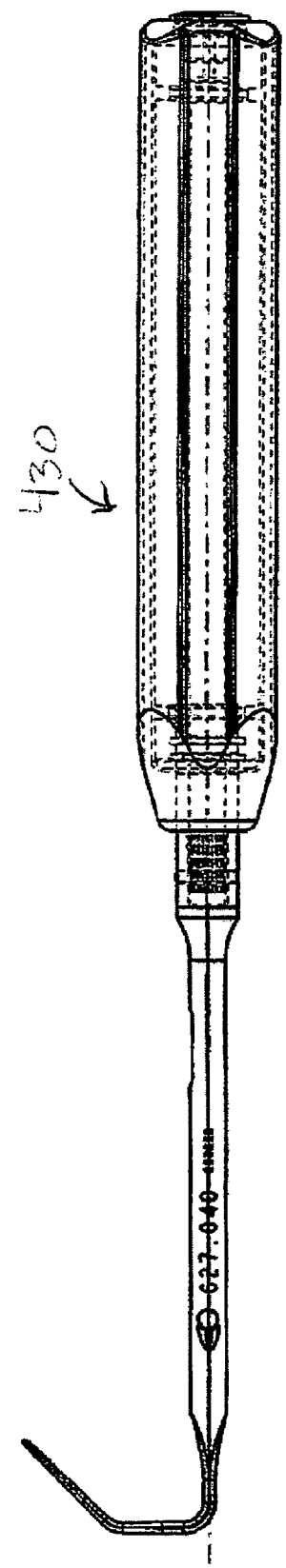

According to one embodiment of a method according to the invention for inserting implant 300, the adjacent first and second spinal processes may be accessed by various methods known by practitioners skilled in the art, for example, by accessing the spinous processes from at least one lateral side/unilateral, bilateral, or midline posterior approach. Certain methods of the present invention include removing or dilating any interspinous ligaments in a position in which the implant is to be placed in the patient prior to inserting the implant. In one exemplary embodiment, a dilation tool 430 as shown in FIGS. 43-44 may be utilized to dilate interspinous ligaments. For example, when using a unilateral approach, dilation tool 430 is particularly well suited to access and/or dilate ligaments on the side of the spinous processes opposite the incision. The bullet or horn shaped end portion 304 further facilitates insertion through the dilation. In this regard, according to certain methods of the invention, a unilateral approach may be used to install implant 300 without removal of the supraspinous ligament.

Figures 45, 46:
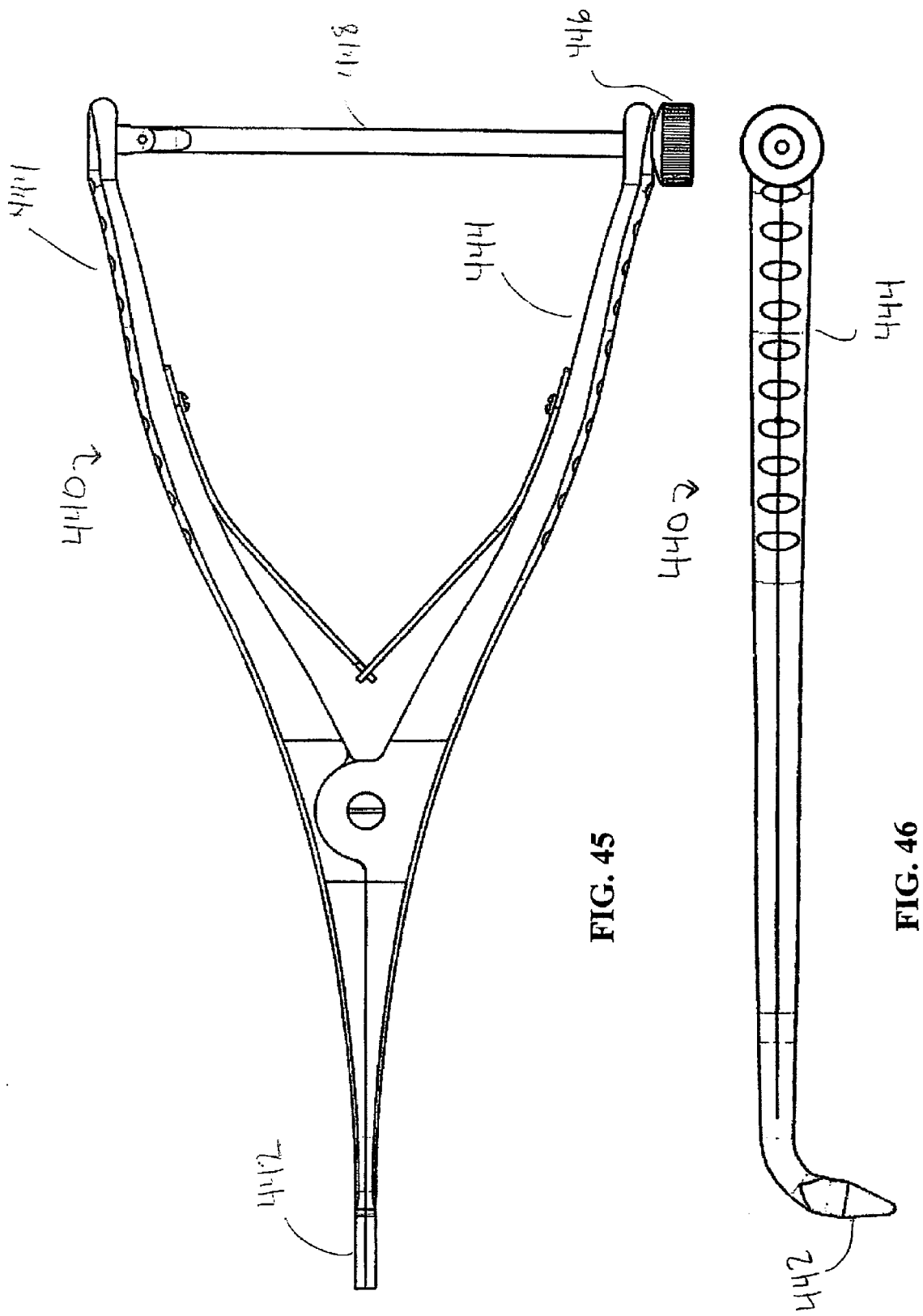
FIGS. 45-46 depict one embodiment of a dilation tool constructed in accordance with the present invention.

Other embodiments of methods of the present invention may include dilating or distracting the spinous processes apart from one another before sizing and/or before inserting the implant. In one exemplary embodiment, a distraction tool 440 as shown in FIGS. 45-46 may be utilized to distract spinous processes. In operation, the distal tips 442 of distraction tool 440 may be inserted between adjacent processes and the handles 444 on the proximal end of the tool may be compressed to cause distal tips 442 to spread apart. As is known in the art, a compression dial 446 and measuring bar 448 may be provided to facilitate measurable and/or precise distraction.

Figure 47:
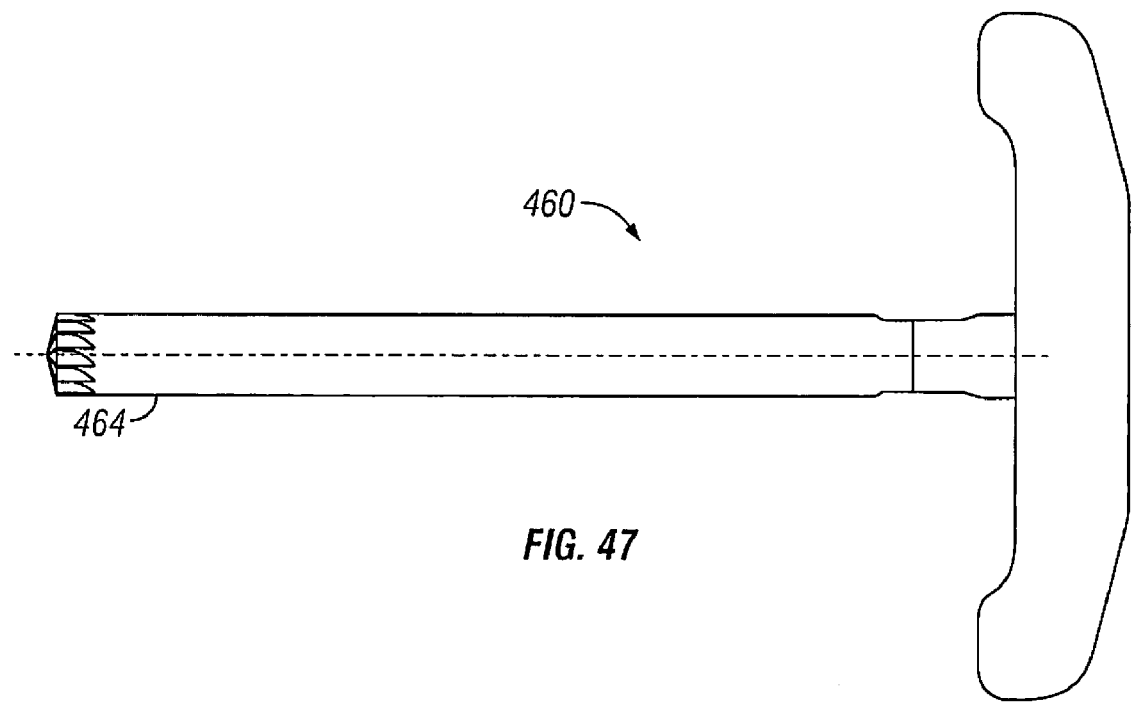
FIGS. 47-48 depict one embodiment of a facet reamer tool constructed in accordance with the present invention.
Figure 48:
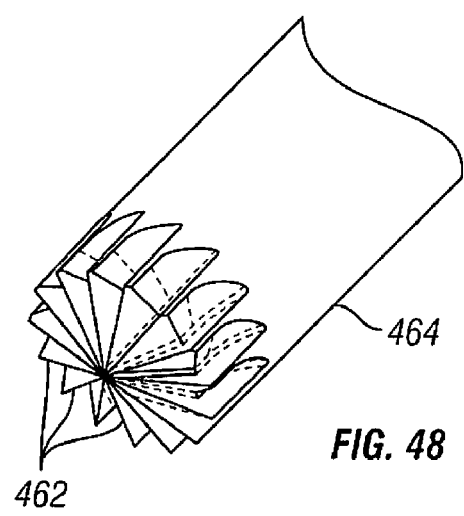
Figure 49:
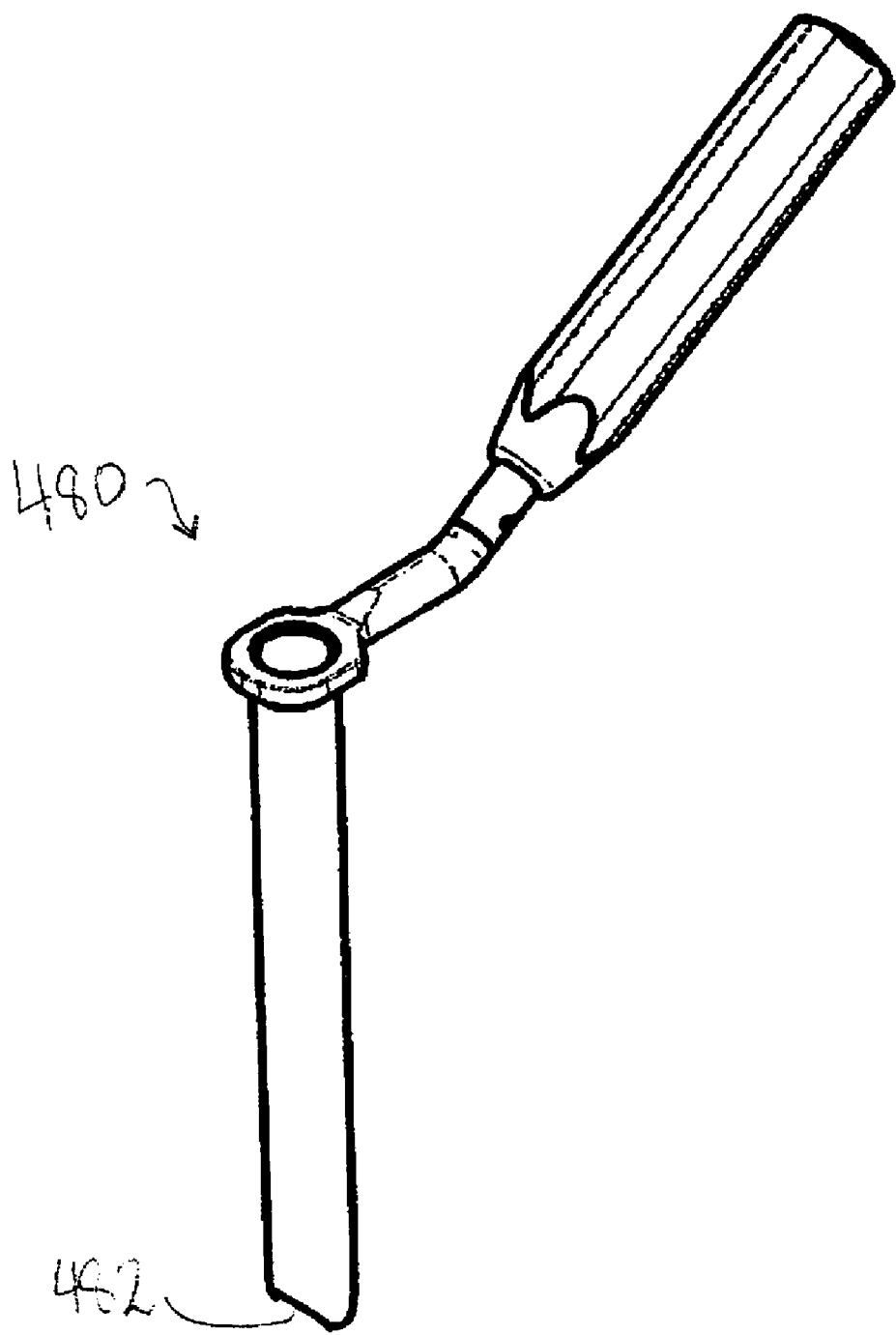
FIG. 49 is a perspective view of one embodiment of a facet reamer sleeve for use with the reamer tool of FIGS. 47-48.
Figure 50:
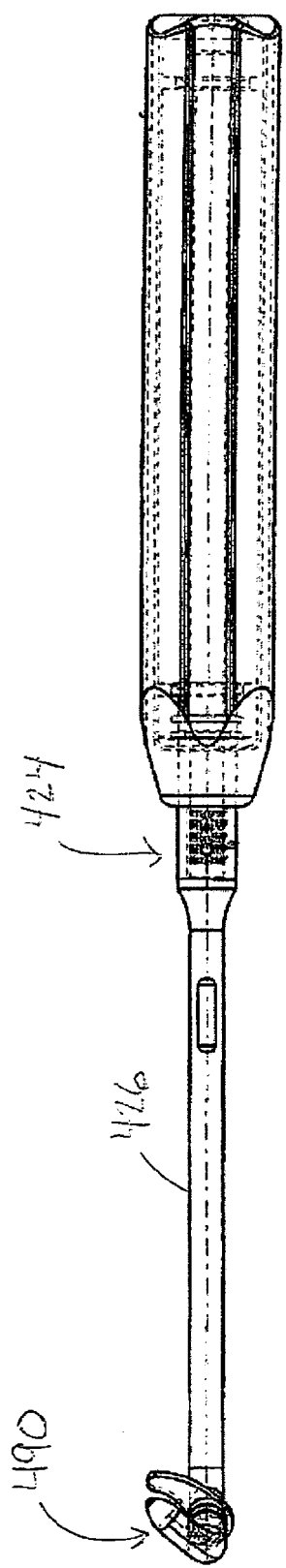
FIGS. 50-52 depict one embodiment of a trial assembly constructed in accordance with the present invention.

In certain methods of installation, it may be desired or necessary to reduce a portion of one or more facet joints adjacent the implantation locale. For example, in some patients inflamed or enlarged facet joints may impede or hinder a surgeon's ability to install an implant between the spinous processes. In one exemplary embodiment, a reamer tool 460 as shown in FIG. 47-48 may be utilized in combination with a guide sleeve 480, shown in FIG. 49, to remove, ream, or otherwise reduce at least a portion of the enlarged facet. In one embodiment, reamer 460 comprises a plurality of fluted cutting surfaces 462 adjacent its distal tip 464. In one variation, cutting surfaces 462 extend radially around distal tip 464. In operation, guide sleeve 480 may be inserted into the patient and the distal tip 482 of the guide sleeve 480 is configured and dimensioned to fit on or engage a bulbous facet to be treated. Reamer tool 460 may then be inserted into sleeve 480 such that distal tip 482 contacts the facet and rotation of reamer tool 460 grinds, cuts, reams or otherwise removes material from the facet joint.

In another embodiment of a method according to the invention, sizing of the space between adjacent spinous processes (for example using trials) may be performed. In one exemplary embodiment, a trial 490 and insertion tool 424, shown in FIGS. 50-52, may be utilized to size the space between adjacent processes. In one variation, trial 490 comprises multiple longitudinal indentations or markings 492 on at least a portion of central portion 494. Markings 492 provide visual indication when viewed under fluoroscopy of the width of the spinous processes and facilitate the surgeon's selection of an appropriately sized implant. Similarly, the appropriate diameter of central portion 494 of trial 490 may be selected to gauge the amount of distraction desired. In this regard, the spacing of the spinous processes may be viewed under fluoroscopy to facilitate the surgeon's selection of an appropriately sized implant. Finally, an implant of the appropriate size may be inserted between the adjacent spinous processes.

While the invention herein disclosed has been described by means of specific embodiments and applications thereof, numerous modifications and variations can be made thereto by those skilled in the art without departing from the scope of the invention.

What is claimed is:

1. A prosthetic device for implantation between adjacent vertebral bodies in a vertebral column, the prosthetic device comprising: a body comprising a central support portion having top, bottom, front and back surfaces, the central support portion extending laterally along a lateral axis between first and second end portions, the first end portion extending longitudinally along a first longitudinal axis and the second end portion extending longitudinally along a second longitudinal axis, and the first and second longitudinal axes are generally perpendicular to the lateral axis, wherein at least a portion of first and second end portions protrude beyond the top and bottom surfaces of the support portion in the cranial-caudal direction, protrude beyond the front and the back surfaces of the support portion in the anterior-posterior direction to further distract at least a portion of the adjacent vertebral bodies of the vertebral column, and wherein the central support portion has first and second concave portions extending from the first end portion to the second end portion on the upper and lower surfaces for supporting the adjacent vertebral bodies and third and fourth concave portions extending from the first end portion to the second end portion on the front and back surfaces for supporting and centering the adjacent vertebral bodies on the central support portion, wherein the second end portion comprises a plate having a uniform thickness and an opening to engage an insertion tool, the opening extending from the second end portion through the central support portion and the first end portion, wherein the second end portion comprises an anterior cutout to accommodate lamina in an implanted position, and wherein the first and second end portions further comprise multiple grooves extending laterally along a portion of the front and back surface of the first and second end portions for preventing movement in any non-parallel direction with respect to spinous processes.

2. The device of claim 1, wherein the body is made from a polyetheretherketone (PEEK) material.

3. The device of claim 1, wherein the body includes a locating pin, the locating pin made from a radio-opaque material.

4. The device of claim 1, wherein the first end portion is curved adjacent a distal end.

5. The device of claim 1, wherein the support portion is configured and dimensioned to fit between adjacent spinous processes and further comprises:
   a proximal support surface spaced longitudinally from a distal support surface by a first distance, the support surfaces configured to contact adjacent spinous processes of the vertebral column, wherein the first distance is predetermined for spacing of two adjacent spinous processes when the device is implanted in the vertebral column.

6. The device of claim 1, wherein the support portion has a generally circular cross-section.

7. The device of claim 1, wherein the support portion has a generally rectangular cross-section.

8. The device of claim 1, wherein at least a portion of the end portions extend longitudinally beyond first and second support surfaces in the longitudinal direction.

9. The device of claim 1, wherein the first and second longitudinal axes are coplanar to the lateral axis.

10. The device of claim 1, wherein the end portions are laterally spaced by a second distance, the second distance generally corresponding to a predetermined distance for accommodating the width of the spinous processes.

11. The device of claim 1, wherein the end portions are configured and dimensioned to contact the lateral sides of the spinous process when the device is implanted in the vertebral column.

12. The device of claim 1, wherein at least one of the end portions define at least one opening for accommodating a fastening device to fasten the device to the spinous process when the device is implanted.

13. The device of claim 1, wherein the body is configured and dimensioned to be rotated in-situ to distract adjacent spinous processes.

14. The device of claim 1, wherein the support portion further comprises a ramp portion adjacent at least one end portion to center the adjacent spinous processes along the central portion.

15. A prosthetic device for implantation in a treated area of an intervertebral space between vertebral bodies of a spine, comprising: a spacer body comprising a central support portion extending along a lateral axis between first and second end portions, the central support portion comprising an anterior surface and a posterior surface, wherein the anterior and posterior surfaces each have a contact area capable of engaging with anatomy in the treated area and the anterior and posterior surfaces are spaced apart a first distraction distance in a first direction, the central support portion comprising an inferior surface and a superior surface, wherein the inferior and superior surfaces each have a contact area capable of engaging with anatomy in the treated area and the inferior and superior surfaces are spaced apart a second distraction distance in a second direction, wherein the first distraction distance is less than the second distraction distance, wherein the central support portion is configured and dimensioned to be positioned between adjacent vertebral bodies, wherein when the device is in a first implantation position the adjacent vertebral bodies are maintained substantially separated by at least the first distraction distance and when the device is in a second implantation position the adjacent vertebral bodies are maintained substantially separated by at least the second distraction distance, wherein the central support portion is rotatable from the first implantation position to the second implantation position, wherein in the first implantation position the first and second end portions are located between the adjacent vertebral bodies, extending in an anterior-posterior direction, wherein in the second implantation position the first and second end portions are located laterally adjacent opposite lateral sides of a portion of the vertebral bodies, extending in a cranial-caudal direction, wherein at least a portion of the contact areas of the anterior and posterior surfaces are concave for engaging the adjacent vertebral bodies and at least a portion of the contact areas of the inferior and superior surfaces are concave for engaging the adjacent vertebral bodies, and wherein at least a portion of first and second end portions protrude beyond the superior and inferior surfaces of the central support portion in a cranial-caudal direction and protrude beyond the anterior and the posterior surfaces of the support portion in an anterior-posterior direction to further distract at least a portion of the adjacent vertebral bodies of the vertebral column, wherein the first and second end portions further comprise multiple grooves extending laterally along a portion of the anterior and the posterior surfaces of the first and second end portions for preventing movement in any non-parallel direction with respect to spinous processes, wherein at least one of the first and second end portions comprise an anterior cutout to accommodate a portion of lamina in the second implantation position.

16. The device of claim 15, wherein the first end portion extends longitudinally along a first longitudinal axis and the second end portion extends longitudinally along a second longitudinal axis, and the first and second longitudinal axes are generally perpendicular to the lateral axis.

17. The device of claim 16, wherein the first end portion is tapered along its longitudinal length.

18. The device of claim 15, wherein the support portion further comprises a ramp portion adjacent at least one end portion to center a portion of the adjacent vertebral bodies along the central portion.

19. A prosthetic device for implantation between adjacent spinous processes in a vertebral column, the prosthetic device comprising:
   a body comprising a central support portion extending laterally along a lateral axis between first and second end portions, the first end portion extending longitudinally along a first longitudinal axis and the second end portion extending longitudinally along a second longitudinal axis, and the first and second longitudinal axes are substantially perpendicular to the lateral axis,
   wherein at least a portion of first and second end portions protrude beyond a top surface and a bottom surface of the support portion in the cranial-caudal direction and protrude beyond a front surface and a back surface of the support portion in the anterior-posterior direction to further distract at least a portion of the adjacent spinous processes of the vertebral column,
   wherein the support portion is configured and dimensioned to fit between adjacent spinous processes and further comprises a concave proximal support surface spaced longitudinally from a distal concave support surface by a first distance, the support surfaces configured to contact and support adjacent spinous processes of the vertebral column, wherein the first distance is predetermined for spacing of two adjacent spinous processes when the device is implanted in the vertebral column, wherein the second end portion comprises an anterior cut-out to accommodate a portion of the Lamina when the device is implanted in the vertebral column and includes at least one opening to accommodate a fastening device to fasten the device to the spinous process when the device is implanted in the vertebral column, and wherein the first and second end portions further comprise multiple grooves extending laterally along a portion of the front and back surface of the first and second end portions for preventing movement in any non-parallel direction with respect to the spinous processes wherein the central support portion comprises proximal indented regions and distal indented regions, the width of the proximal indented regions being different than the width of the distal indented regions.

* * * * *